(12) United States Patent
Thiele

(10) Patent No.: US 7,915,194 B2
(45) Date of Patent: Mar. 29, 2011

(54) PROCESS FOR HOMO- OR COPOLYMERIZATION OF CONJUGATED OLEFINS

(75) Inventor: Sven K. H. Thiele, Halle (DE)

(73) Assignee: Styron Europe GmbH, Horgen (CH)

( * ) Notice: Subject to any disclaimer, the term of this patent is extended or adjusted under 35 U.S.C. 154(b) by 0 days.

(21) Appl. No.: 12/557,121

(22) Filed: Sep. 10, 2009

(65) Prior Publication Data

US 2010/0248947 A1   Sep. 30, 2010

Related U.S. Application Data

(62) Division of application No. 10/543,986, filed as application No. PCT/US2004/004941 on Feb. 18, 2004, now Pat. No. 7,612,009.

(60) Provisional application No. 60/449,076, filed on Feb. 21, 2003, provisional application No. 60/449,077, filed on Feb. 21, 2003.

(51) Int. Cl.
*B01J 31/22* (2006.01)
*B01J 31/14* (2006.01)
*C08F 4/52* (2006.01)

(52) U.S. Cl. ........ 502/167; 502/103; 502/120; 526/129; 526/135; 526/161; 526/164; 526/165; 526/335; 526/340

(58) Field of Classification Search .................. 502/103, 502/120, 167; 526/129, 135, 161, 164
See application file for complete search history.

(56) References Cited

OTHER PUBLICATIONS

Lorenz et al., "Between Enamide and Azaallyl Structures: Novel Flexible N-Chelate Ligands in the Lanthanide Chemistry", Organometallics, 2005.*

* cited by examiner

Primary Examiner — Caixia Lu

(74) Attorney, Agent, or Firm — Brinks Hofer Gilson & Lione

(57) ABSTRACT

Metal complexes, catalyst compositions containing the metal complexes, and processes for making the metal complexes and the catalyst compositions are described for the manufacture of polymers from ethylenically unsaturated addition polymerizable monomers. The metal complexes have chemical structures corresponding to one of the following formulae:

Formula Ia

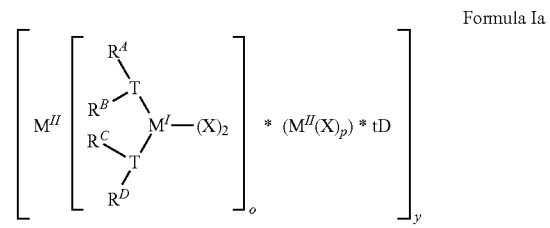

Formula Ib

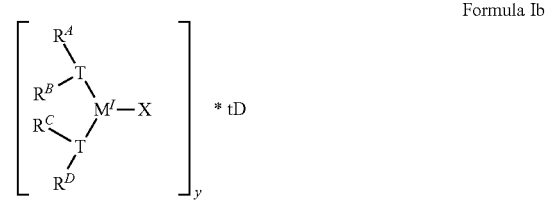

Formula VII
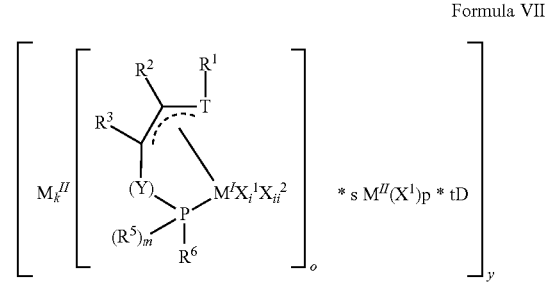

wherein $M^I$ and $M^{II}$ are metals; T is nitrogen or phosphorus; P is a carbon, nitrogen or phosphorus atom; groups $R^1$, $R^2$ and $R^3$ may be linked to each other; Y is a divalent bridging group; X, $X^1$, and $X^2$ are anionic ligand groups with certain exceptions; D is a neutral Lewis base ligand; and s, o, k, i, ii, p, m, a, b, c, d, e, t, and y are numbers as further described in the claims.

8 Claims, No Drawings

PROCESS FOR HOMO- OR COPOLYMERIZATION OF CONJUGATED OLEFINS

This application is a divisional of U.S. application Ser. No. 10/543,986, filed Jul. 29, 2005 U.S. Pat. No. 7,612,009 which is U.S. National Stage Application, under 35 U.S.C. §371, of International Application No. PCT/US2004/004941, filed on Feb. 18, 2004, now allowed, which claims the benefit of U.S. Provisional Application No. 60/449,076, filed on Feb. 21, 2003, and U.S. Provisional Application No. 60/449,077, filed on Feb. 21, 2003.

This invention relates to metal complex compositions, their preparation and their use as catalysts to produce polymers through (homo)polymerization of ethylenically unsaturated addition polymerizable monomers or through copolymerization of ethylenically unsaturated addition polymerizable monomers with at least one different type of ethylenically unsaturated addition polymerizable monomer.

More particularly, this invention relates to metal complex compositions, their preparation and their use as catalysts to produce polymers of conjugated dienes through polymerization of conjugated ethylenically unsaturated addition polymerizable monomers or through copolymerization of conjugated ethylenically unsaturated addition polymerizable monomers with at least one different type of ethylenically unsaturated addition polymerizable monomer.

The used metal complex compositions are group 3 metal compounds including lanthanides and actinides, preferably lanthanide compounds, more preferably neodymium compounds in combination with activator compound(s) and optionally a catalyst support.

More particularly, the invention relates to metal complexes containing at least one metal-nitrogen or metal-phosphorus bond and in addition to it at least one metal halide bond, more particularly at least one metal-nitrogen bond and at least one metal halide bond and to the preparation of the catalyst and the use of the prepared catalyst to produce homo- or copolymers of conjugated dienes, preferably through, but not limited to, through homopolymerization of 1,3-butadiene or copolymerization of 1,3-butadiene with styrene or isoprene. More preferably the polydiene or the polydiene sequences of the copolymer consist predominantly of cis units.

Polymers from conjugated ethylenically unsaturated addition polymerizable monomers and metal complex catalysts for producing the same are known.

Knowledge of the molecular weight and molecular weight distribution of the polymer as well as the microstructure of the polydiene part, for example the cis-1,4-, trans-1,4- and 1,2-polybutadiene ratio in case of polybutadiene, is crucial for the preparation of polymers with desired properties. Though a few patents describe some characteristics of the polydiene obtained, little effort was made to improve the polymerization activity and to change the molecular weight of the polymer while maintaining the interesting polymer cis selectivity.

It would be valuable to recognize that the kind and arrangement of the ligand on the metal complex can have a dominating effect on the polymer microstructure while different mixtures of the metal complex (precatalyst) with the co-catalyst can have a dominant effect on the molecular weight of the polymer and on the polymerization activity of the polymerization reaction. The desired high cis selectivity of the polydiene could be achieved by selecting suitable precatalysts in combination with specific activators while the exchange of the precatalysts under identical reaction conditions including the activator component leads to higher trans fractions. On the other hand it is desirable to tune the molecular weight of the polydienes and the polymerization activity of the polymerization reaction by selecting suitable types and amounts of co-catalysts. In addition, there is a need for catalyst precursors and catalysts which are stable in a dry state and in solution at room temperature and at is higher temperatures so that these compounds may be more easily handled and stored. In addition, it would be desirable to have catalyst components that could be directly injected into the polymerization reactor without the need to "age" (stir, shake or store) the catalyst or catalyst components for a longer period of time. Especially for a solution polymerization process or a continuous polymerization process, liquid or dissolved catalyst or catalyst components are more suitable for a proper dosing into the polymerization vessel. Furthermore, it is highly desirably to have a highly active polymerization catalyst for conjugated dienes which is stable and efficient in a broad temperature range for a longer period without deactivation. It also would be beneficial if polydienes with high cis contents and high molecular weight could be produced efficiently. High molecular weight polybutadienes with a high fraction of cis-1,4-polybutadiene are interesting materials for the production of tire tread and side walls.

According to the present invention for the polymerization of one type of ethylenically unsaturated addition polymerizable monomer or the copolymerization of one type of ethylenically unsaturated addition polymerizable monomer with at least one different type of ethylenically unsaturated addition polymerizable monomer there are provided metal complexes.

In one embodiment according to the current invention there are provided metal complexes corresponding to one of the Formulae Ia and Ib:

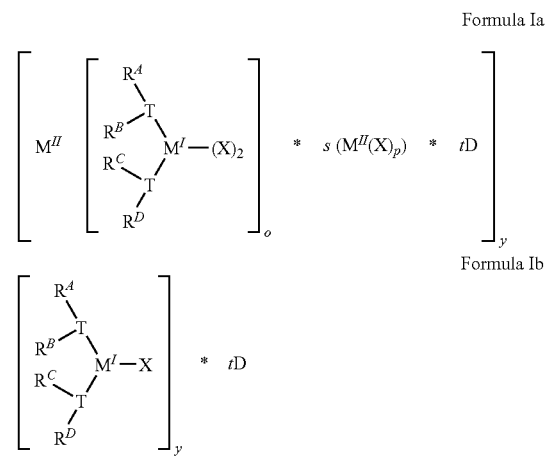

wherein:
$M^I$ is lanthanum, cerium, praseodymium, neodymium, promethium or a metal from Group 3 of the Periodic Table of the Elements, or the actinides;
$M^{II}$ is a metal from one of the Groups 1 or 2 of the Periodic Table of the Elements
T is nitrogen or phosphorus;
$R^A$, $R^B$, $R^C$ and $R^D$ independently each occurrence are hydrogen or a group having from 1 to 80 atoms not counting hydrogen, which is hydrocarbyl, hydrocarbylsilyl, halo-substituted hydrocarbyl, hydrocarbyloxy-substituted is hydrocarbyl, hydrocarbylamino-substituted hydrocarbyl, or hydrocarbylsilyl-substituted hydrocarbyl;

wherein neither of the groups $R^A$ and/or $R^B$ are linked to either of the groups $R^C$ and/or $R^D$, except by means of the T-MIT linking group;

X independently each occurrence is an anionic ligand group having up to 60 atoms, provided however that in no occurrence is X an amide group, a phosphide group, a cyclic, delocalized, aromatic group that is π-bonded to $M^I$ or $M^{II}$ or a allylic delocalized group that is π-bonded to $M^I$ or $M^{II}$;

D independently each occurrence is a neutral Lewis base ligand having up to 30 nonhydrogen atoms;

s is the number 0 or 1;

o is the number 1 or 2;

p is the number 1, 2, 3 or 4;

t is one of the numbers 0 to 5; and y is one of the numbers 1 to 20.

The formula weight of the metal complex is preferably lower than 25,000 g/mol, more preferably lower than 20,000 g/mol.

Additionally according to the present invention there are provided metal complexes resulting from the combination of one equivalent of a Group 3 metal, lanthanide or actinide compound corresponding to Formula II with more than one and less than three equivalents of the group 1 or group 2 complexes corresponding to Formula IIIa and/or IIIb:

              Formula II

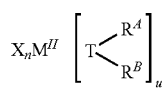              Formula IIIa

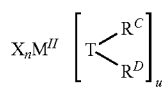              Formula IIIb wherein $M^I$, $M^{II}$, T, $R^A$, $R^B$, $R^C$, $R^D$, t, D, and X are as previously defined;

n is the number zero or 1; and u is the number one or two.

Additionally, according to the present invention there is provided a process for preparing metal complexes corresponding to one of the Formulas Ia and Ib wherein $M^I$, $M^{II}$, T, $R^A$, $R^B$, $R^C$, $R^D$, X, D, o, s, p, t and y are as previously defined and wherein neither of the groups $R^A$ and/or $R^B$ are linked to either of the groups $R^C$ and/or $R^D$, except by means of the T-$M^I$-T linking group comprising contacting a compound according to Formula II wherein $M^I$, X, t and D are as previously defined with more than one and less than three equivalents of the group 1 or group 2 compounds corresponding to Formula IIIa and/or IIIb wherein $M^I$, $M^{II}$, T, $R^A$, $R^B$, $R^C$, $R^D$, t, D, and X are as previously defined, n is the number zero or 1, and u is the number one or two.

In another embodiment according to the present invention there are provided metal complexes corresponding to one of the formula VII:

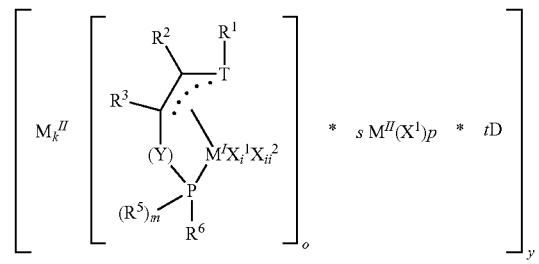

Formula VII wherein:

$M^I$ is a metal from Group 3, 4 or 5 of the Periodic Table of the Elements, a lanthanide metal or an actinide metal;

$M^{II}$ is a metal from one of the Groups 1 or 2 of the Periodic Table of the Elements T is nitrogen or phosphorus;

P is a carbon atom, a nitrogen atom or a phosphorus atom $R^1$, $R^2$, $R^3$, $R^5$ and $R^6$ independently each occurrence are hydrogen, a halide atom or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl; and the groups $R^1$, $R^2$ and $R^3$ may be linked to each other;

Y is a divalent bridging group joining two groups wherein Y is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, preferably Y is $(CR^{11}_2)_a$ or $(CR^{13}_2)_bO(CR^{14}_2)_c$. or $(CR^{15}_2)_dS(CR^{16}_2)_e$. or 1,2-disubstituted aromatic ring system wherein $R^{11}$, $R^{13}$, $R^{14}$, $R^{15}$ and $R^{16}$ are a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl;

$X^1$, $X^2$ independently each occurrence are anionic ligand groups having up to 60 atoms, provided however that in no occurrence is $X^1$ or $X^2$ a delocalized, aromatic group that is π-bonded to M or a allylic delocalized group that is π-bonded to M;

D independently each occurrence is a neutral Lewis base ligand having up to 30 nonhydrogen atoms;

s is the number 0, 1, 2, 3 or 4 (preferably 0, 1, 3 or 4);

o is the number 1 or 2;

k is the number 0, 1, 2, 3 or 4;

i, ii independently each occurrence are the numbers 0, 1, 2, 3 or 4;

p is the number 1 or 2;

m is the numbers 0 or 1;

a, b, c, d and e independently each occurrence are the numbers 1, 2, 3 or 4;

t is one of the numbers 0 to 5; and y is one of the numbers 1 to 20.

i and ii independently each occurrence are preferably the numbers 0, 1, 2 or 3; and preferably the sum of i and ii represents one of the numbers 1, 2, 3 or 4 and, thus may not be zero (i+ii☐0).

The formula weight of the metal complex preferably is lower than 25,000 g/mol, more preferably lower than 20,000 g/mol.

Additionally according to the present invention there are provided metal complexes resulting from the reaction of a compound corresponding to formula VIII with a compound corresponding to formula IX:

$$M^I(X^1)_3 * tD \qquad \text{Formula VIII}$$

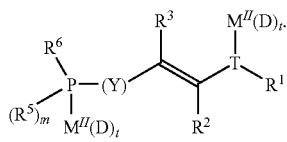

Formula IX wherein $M^I$, $M^{II}$, T, $R^1$, $R^2$, $R^3$, $R^5$, $R^6$, Y, P, D, $X^1$, m and t are as previously defined.

Additionally, according to the present invention there is provided a process for preparing metal complexes corresponding to one of the formulas VIIIa, VIIb and VIIc:

Formula VIIa

Formula VIIb

Formula VIIc wherein
$M^{II}$, T, $R^1$, $R^2$, $R^3$, $R^4$, $R^5$, $R^6$, Y, P, D, $X^1$, $X^2$, k, s, p, t, o and y are as previously defined, $M^I$ is a metal from Group 3 of the Periodic Table of the Elements, a lanthanide metal or an actinide metal;

i and ii independently each occurrence are as defined above, and are preferably the numbers 0, 1, 2 or 3; and preferably the sum of i and ii represents one of the numbers 1, 2, 3 or 4 and, thus may not be zero
(i+ii≠0); and C is a carbon atom; comprising:
contacting a compound according to formula VIII:

$$M^I(X^1)_3 * tD \qquad \text{Formula VIII}$$

wherein $M^I$, D, t and $X^1$ are as previously defined, with one of the compounds corresponding to formula IXa, IXb or IXc:

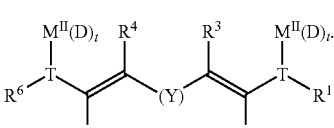

Formula IXa

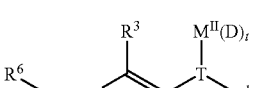

Formula IXb

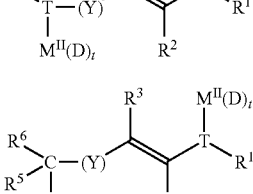

Formula IXc wherein $M^{II}$, T, $R^1$, $R^2$, $R^3$, $R^4$, $R^5$, $R^6$, Y, D, and t are as previously defined and C is a carbon atom.

Preferably according to the invention $X^1$ is a fluoride, chloride, bromide or iodide atom and T is a nitrogen atom.

Even more preferably $M^{II}$ is an atom of group 1 of the Periodic Table of the Elements.

In a preferred embodiment, the compound according to the formula VIII $$M^I(X^1)_3 * tD \qquad \text{Formula VIII}$$

wherein $M^I$, D and t are as previously defined and $X^1$ groups are fluoride, chloride, bromide or iodide, or a hydrocarbyl group, a hydrocarbylsilyl group, a halo-substituted is hydrocarbyl group, or an —OR group, wherein R independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, is contacted with compounds according to one of the formulas IXd/e or IXf:

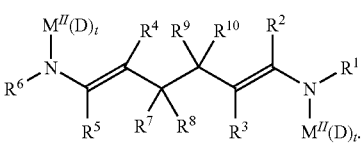

Formula IXd/e

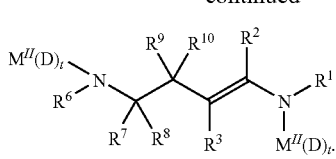

Formula IXf wherein $M^{II}$, $R^1$, $R^2$, $R^3$, $R^4$, $R^5$, $R^6$, D, N and t are as previously defined and $R^7$, $R^8$, $R^9$ and $R^{10}$ independently each occurrence are hydrogen, a halide atom or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl; in a solvent.

In a preferred embodiment, one equivalent of the compound according to the formula VIII, $$M^I(X^1)_3 * tD \qquad \text{Formula VIII}$$

wherein D and t are as previously defined, $M^I$ is a lanthanide metal; $X^1$ is a fluoride, is chloride, bromide or iodide atom is contacted with one of the compounds corresponding to formula IXd/e and IXf (see above) wherein $M^{II}$, $R^1$, $R^2$, $R^3$, $R^4$, $R^5$, $R^6$, D, N and t are as previously defined and $R^7$, $R^8$, $R^9$ and $R^{10}$ independently each occurrence are hydrogen, a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl; in a solvent.

Preferably according to the invention $M^I$ is one of the metals neodymium, lanthanum, cerium, praseodymium, promethium, samarium, europium, gadolinium, terbium or dysprosium; even more preferably $M^I$ is neodymium.

The above-described are useful for the polymerization of one type of ethylenically unsaturated addition polymerizable monomer or the copolymerization of one type of ethylenically unsaturated addition polymerizable monomer with at least one different type of ethylenically unsaturated addition polymerizable monomer as further described below.

Further according to the present invention there are provided catalysts for the polymerization of one type of ethylenically unsaturated addition polymerizable monomer or the copolymerization of one type of ethylenically unsaturated addition polymerizable monomer with at least one different type of ethylenically unsaturated addition polymerizable monomer comprising:

1) a combination of one or more of the above metal complexes and one or more activators (cocatalysts) and optionally a support (carrier material) or
2) the reaction product formed by contacting one or more of the above metal complexes with one or more activators and optionally a support or
3) the product formed by subjecting one or more of the above metal complexes and optionally a support to activating techniques.

The present invention also provides a process for preparing catalysts for the polymerization of one type of ethylenically unsaturated addition polymerizable monomer or copolymerization of one type of ethylenically unsaturated addition polymerizable monomer with at least one different type of ethylenically unsaturated addition polymerizable monomer comprising (1) contacting one or more of the above metal complexes with one or more activators and optionally a support or (2) subjecting one or more of the above metal complexes and optionally a support to activating techniques.

The present invention also provides a polymerization process comprising contacting one or more ethylenically unsaturated addition polymerizable monomers optionally in the presence of an inert, aliphatic, alicyclic or cyclic or aromatic hydrocarbon, under polymerization conditions with a catalyst comprising:

1) a combination of one or more of the above metal complexes and one or more activators and optionally a support or
2) the reaction product formed by contacting one or more of the above metal complexes with one or more activators and optionally a support or
3) the product formed by subjecting one or more of the above metal complexes and optionally a support to activating techniques.

The polymerization may be performed under solution, suspension, slurry, or gas phase process conditions, and the catalyst or individual components thereof may be used in a heterogeneous, that is, a supported state, or in a homogeneous state as dictated by process conditions. The catalyst can be used in combination with one or more additional catalysts of the same or different nature either simultaneously or sequentially in the same reactor and/or sequentially in separate reactors. The catalyst can be formed in situ in the presence of, or prior to addition to, a reaction mixture comprising one or more ethylenically unsaturated addition polymerizable monomers.

According to the present invention there are provided homopolymers comprising one ethylenically unsaturated addition polymerizable monomer, even more especially one conjugated ethylenically polyunsaturated addition polymerizable monomer.

Further according to the present invention there are provided copolymers is comprising more than one ethylenically unsaturated addition polymerizable monomer, even more especially conjugated ethylenically polyunsaturated addition polymerizable monomers in combination with a second type of ethylenically unsaturated addition polymerizable monomer.

Catalysts for polymerization of ethylenically unsaturated addition polymerizable monomers, preferably catalysts for polymerization of conjugated ethylenically polyunsaturated addition polymerizable monomers, according to the invention possess improved catalytic properties and are especially useful in the polymerization of conjugated dienes. In addition, the complexes are compatible with and may be used in combination with alkylaluminum compounds which may be employed to scavenge monomer impurities without detrimental effects to their catalytic properties.

The homopolymers and copolymers of the invention may be used in the production of many useful shapes, molded parts, films, foams, golf balls, tires, hoses, conveyor and other belts, gaskets, seals, shoes and in the modification of plastics.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

By the term "neutral Lewis base ligand" is meant uncharged groups that are sufficiently nucleophilic to be capable of forming a coordination bond to the metal atom of the metal complex of the invention. Preferred neutral Lewis base ligand groups, D, are carbon monoxide, acetylacetonate, ethers, thioethers, polyethers, amines, polyamines, phosphines, phosphites, polyphosphines, alcohols, nitriles, esters, olefins and conjugated dienes. The metal complexes according to the present invention may be present as coordination complexes of neutral Lewis base ligands.

In the preferred metal complexes according to the present invention corresponding to one of the Formulas IVa or IVb:

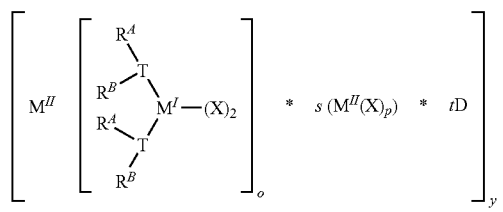

Formula IVa

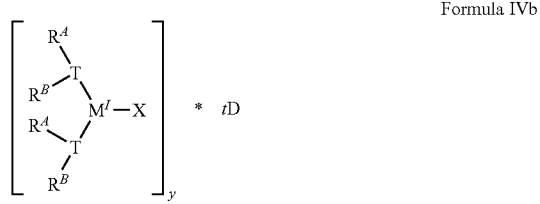

Formula IVb wherein:

$M^{II}$ is a metal from one of the Groups 1 or 2 of the Periodic Table of the Elements;

T is nitrogen or phosphorus;

$M^I$ comprises lanthanum, cerium, praseodymium, neodymium, or promethium;

$R^A$ and $R^B$ are hydrocarbyl, especially alkyl, cyclic alkyl, aryl, alkaryl, more especially methyl, ethyl, 1-methylethyl, 1,1-dimethylethyl, cyclohexyl, phenyl, 2,6-dialkylphenyl, benzyl, trimethylsilyl and hydrocarbylsilyl; and the two ligands $(R^A)(R^B)T$ are not linked to each other in any way, except by means of the MI linking group;

D independently each occurrence is selected from carbon monoxide; phosphines, $PR^i_3$, and phosphites, $P(OR^i)_3$, wherein $R^i$ independently each occurrence is hydrocarbyl, silyl, especially trimethylphosphine, triethylphosphine, tributylphosphine, triphenylphosphine and 1,2-bis(dimethylphosphino)ethane, 1,2-bis(diphenylphosphino)ethane, bis (diphenylphosphino)methane, 1,3-bis(diphenylphosphino) propane, trimethylphosphite, triethylphosphite, tributylphosphite, triphenylphosphite; thioethers, especially dimethylthioether, methylphenylthioether, diethylthioether; ethers and polyethers, especially tetrahydrofuran (THF), diethylether (Et₂O), dioxane, 1,2-dimethoxyethane (DME); amines and polyamines, especially pyridine, bipyridine, pyrrolidine, piperidine, tetramethylethylenediamine (TMEDA) and triethylamine (TEA); olefins, especially ethylene, propylene, butene, hexene, octene, styrene, divinylbenzene; conjugated dienes having from 4 to 40 carbon atoms, especially butadiene, isoprene, 1,3-pentadiene, 2,4-hexadiene; alcohols, especially methanol, ethanol, propanol, butanol; nitriles, especially acetonitrile, acrylonitrile, propanenitrile, benzonitrile; esters, especially methyl acetate, ethyl acetate, butyl acetate, methyl acrylate, methyl methacrylate, methyl benzoate;

X groups are fluoride, chloride, bromide or iodide, or a hydrocarbyl group, a hydrocarbylsilyl group, a halo-substituted hydrocarbyl group, or an —OR group, wherein R independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, and more preferred groups are fluoride, chloride, bromide or iodide;

s is the number 0 or 1;

o is the number 1 or 2;

p is the number 1, 2, 3 or 4;

t is one of the numbers 0 to 3; and y is the number 1, 2, 3, 4, 5, 6, 7, 8, 9 or 10.

The formula weight of the metal complex preferably is lower than 20,000 g/mol, more preferably lower than 15,000 g/mol.

Preferably, $M^I$ comprises lanthanum, cerium, praseodymium, neodymium, promethium; even more preferably neodymium.

Preferably, $M^{II}$ comprises a lithium, sodium, potassium or magnesium atom.

T preferably comprises nitrogen.

Preferably, D comprises tetrahydrofuran (THF), diethylether (Et₂O), dioxane, 1,2-dimethoxyethane (DME).

Preferably X is a fluoride, chloride, bromide or iodide atom and T is a nitrogen atom.

Even more preferably $M^{II}$ is an atom of Group 1 of the Periodic Table of the Elements; and n is the number zero.

Even more preferably $R^A$ and $R^C$ are selected to be identical and $R^B$ and $R^D$ are selected to be identical.

In a preferred embodiment, the compound according to the Formula II wherein the X groups are fluoride, chloride, bromide or iodide, or a hydrocarbyl group, a hydrocarbylsilyl group, a halo-substituted hydrocarbyl group, or an —OR group, wherein R independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, is contacted with more than one and less than three equivalents of the Group 1 or Group 2 compounds according to the Formulae IIIa and IIIb, in a solvent.

Preferred metal complexes according to the present invention are metal complexes resulting from the reaction of one equivalent of a Group 3 metal, lanthanide or actinide compound corresponding to Formula II with more than 1.5 and less than 2.5 equivalents of the Group 1 compound(s) corresponding to Formula IIIc:

Formula IIIc wherein $M^I$, $M^{II}$, T, $R^A$, $R^B$, t, D, and X are as previously defined and T is preferably nitrogen.

Especially preferred metal complexes according to the present invention correspond to the Formula Va or Vb:

Formula Va

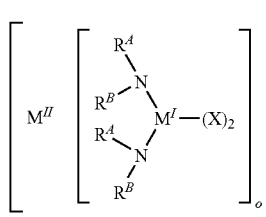

Formula Vb

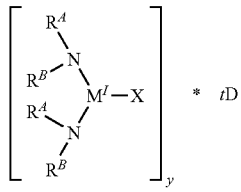

wherein $R^A$, $R^B$ and t are as previously defined;

$M^I$ is lanthanum, cerium, praseodymium, neodymium, promethium;

N is nitrogen;

$M^{II}$ is a metal of group 1 of the Periodic Table of the Elements, especially $M^{II}$ is lithium, sodium or potassium;

X independently each occurrence is fluoride, chloride, bromide or iodide or an —OR group, wherein R independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, and more preferred groups are fluoride, chloride, bromide or iodide;

D is THF, DME, TEA, TMEDA, $Et_2O$;

o is the number 1;

p is the number 1;

s is the number 0 or 1; and y is the number 1, 2, 3, 4, 5, or 6; and the two ligands $(R^A)(R^B)N$ are not linked to each other in any way, except by means of the $M^I$ linking group.

The formula weight of the metal complex preferably is lower than 15,000 g/mol, more preferably lower than 9,000 g/mol.

Especially preferred metal complexes according to the present invention are metal complexes resulting from the reaction of one equivalent of a lanthanide compound corresponding to Formula II with more than 1.5 and less than 2.5 equivalents of the Group 1 compound(s) corresponding to Formula IIIc wherein $M^{11}$ is a group 1 metal.

In an even preferred embodiment, one equivalent of the compound according to the formula II, wherein $M^I$ is neodymium, t and D are as previously defined and X is a fluoride, chloride, bromide or iodide atom, is contacted with more than 1.5 and less than 2.5 equivalents of the Group 1 compound corresponding to Formula IIIc, wherein $R^A$ and $R^B$ are as previously defined and $M^{II}$ is an atom of Group 1 of the Periodic Table of the Elements, in a solvent.

Most highly preferred metal complexes according to the present invention correspond to the Formula VIa or VIb:

Formula VIa

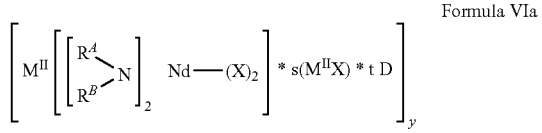

Formula VIb

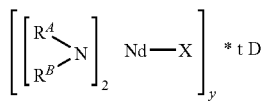

wherein $R^A$ and $R^B$ are alkyl, cyclic alkyl, aryl, alkaryl, more especially methyl, ethyl, 1-methylethyl, 1,1-dimethylethyl, cyclohexyl, phenyl, 2,6-dialkylphenyl, benzyl, trimethylsilyl and benzyl(dimethyl)silyl, t-butyl(dimethyl)silyl, n-butyl(dimethyl)silyl; and $R^A$ and $R^B$ are not connected with each other, except by means of the N linking group;

Nd is neodymium;

$M^{II}$ is lithium, sodium or potassium;

X is fluoride, chloride, bromide or iodide;

D is THF, DME or $Et_2O$;

t is the number 0, 1, 2 or 3;

s is the number 0;

y is the number 1, 2, 3 or 4; and the formula weight of the metal complex preferably is lower than 6,000 g/mol.

Preferably the metal complex does not contain hapto-5 bond ligands such as, but not limited to, cyclopentadienyl, indenyl or fluorenyl ligands, as well as hapto-3 bond ligands such as, but not limited to, allyl or pentadienyl ligands.

Exemplary, but non-limiting metal complexes according to the invention include the following neodymium complexes:
lithium[bis(N,N-diisopropylamido) difluoro neodymate];
lithium [bis(N,N-diisopropylamido) dichloro neodymate];
lithium [bis(N,N-diisopropylamido) dibromo neodymate];
lithium [bis(N,N-diisopropylamido) diiodo neodymate];
sodium [bis(N,N-diisopropylamido) difluoro neodymate];
sodium [bis(N,N-diisopropylamido) dichloro neodymate];
sodium [bis(N,N-diisopropylamido) dibromo neodymate];
sodium [bis(N,N-diisopropylamido) diiodo neodymate];
potassium [bis(N,N-diisopropylamido) difluoro neodymate];
potassium [bis(N,N-diisopropylamido) dichloro neodymate];
potassium [bis(N,N-diisopropylamido) dibromo neodymate];
potassium [bis(N,N-diisopropylamido) diiodo neodymate];
lithium [bis(N,N-dipropylamido) difluoro neodymate];
lithium [bis(N,N-dipropylamido) dichloro neodymate];
lithium [bis(N,N-dipropylamido) dibromo neodymate];
lithium [bis(N,N-dipropylamido) diiodo neodymate];
sodium [bis(N,N-dipropylamido) difluoro neodymate];
sodium [bis(N,N-dipropylamido) dichloro neodymate];
sodium [bis(N,N-dipropylamido) dibromo neodymate];
sodium [bis(N,N-dipropylamido) diiodo neodymate];
potassium [bis(N,N-dipropylamido) difluoro neodymate];
potassium [bis(N,N-dipropylamido) dichloro neodymate];
potassium [bis(N,N-dipropylamido) dibromo neodymate];
potassium [bis(N,N-dipropylamido) diiodo neodymate];
lithium [bis(N,N-diethylamido) difluoro neodymate];
lithium [bis(N,N-diethylamido) dichloro neodymate];
lithium [bis(N,N-diethylamido) dibromo neodymate];
lithium [bis(N,N-diethylamido) diiodo neodymate];
sodium [bis(N,N-diethylamido) difluoro neodymate];
sodium [bis(N,N-diethylamido) dichloro neodymate];
sodium [bis(N,N-diethylamido) dibromo neodymate];

sodium [bis(N,N-diethylamido) diiodo neodymate];
potassium [bis(N,N-diethylamido) difluoro neodymate];
potassium [bis(N,N-diethylamido) dichloro neodymate];
potassium [bis(N,N-diethylamido) dibromo neodymate];
potassium [bis(N,N-diethylamido) diiodo neodymate];
lithium [bis(N-ethylmethylamido) difluoro neodymate];
lithium [bis(N-ethylmethylamido) dichloro neodymate];
lithium [bis(N-ethylmethylamido) dibromo neodymate];
lithium [bis(N-ethylmethylamido) diiodo neodymate];
sodium [bis(N-ethylmethylamido) difluoro neodymate];
sodium [bis(N-ethylmethylamido) dichloro neodymate];
sodium [bis(N-ethylmethylamido) dibromo neodymate];
sodium [bis(N-ethylmethylamido) diiodo neodymate];
potassium [bis(N-ethylmethylamido) difluoro neodymate];
potassium [bis(N-ethylmethylamido) dichloro neodymate];
potassium [bis(N-ethylmethylamido) dibromo neodymate];
potassium [bis(N-ethylmethylamido) diiodo neodymate];
lithium [bis(N,N-dimethylamido) difluoro neodymate];
lithium [bis(N,N-dimethylamido) dichloro neodymate];
lithium [bis(N,N-dimethylamido) dibromo neodymate];
lithium [bis(N,N-dimethylamido) diiodo neodymate];
sodium [bis(N,N-dimethylamido) difluoro neodymate];
sodium [bis(N,N-dimethylamido) dichloro neodymate];
sodium [bis(N,N-dimethylamido) dibromo neodymate];
sodium [bis(N,N-dimethylamido) diiodo neodymate];
potassium [bis(N,N-dimethylamido) difluoro neodymate];
potassium [bis(N,N-dimethylamido) dichloro neodymate];
potassium [bis(N,N-dimethylamido) dibromo neodymate];
potassium [bis(N,N-dimethylamido) diiodo neodymate];
lithium [bis(N,N-dimethylamido) difluoro neodymate];
lithium [bis(N,N-dimethylamido) dichloro neodymate];
lithium [bis(N,N-dimethylamido) dibromo neodymate];
lithium [bis(N,N-dimethylamido) diiodo neodymate];
sodium [bis(N,N-dimethylamido) difluoro neodymate];
sodium [bis(N,N-dimethylamido) dichloro neodymate];
sodium [bis(N,N-dimethylamido) dibromo neodymate];
sodium [bis(N,N-dimethylamido) diiodo neodymate];
potassium [bis(N,N-dimethylamido) difluoro neodymate];
potassium [bis(N,N-dimethylamido) dichloro neodymate];
potassium [bis(N,N-dimethylamido) dibromo neodymate];
potassium [bis(N,N-dimethylamido) diiodo neodymate];
lithium [bis(N,N-diisobutylamido) difluoro neodymate];
lithium [bis(N,N-diisobutylamido) dichloro neodymate];
lithium [bis(N,N-diisobutylamido) dibromo neodymate];
lithium [bis(N,N-diisobutylamido) diiodo neodymate];
sodium [bis(N,N-diisobutylamido) difluoro neodymate];
sodium [bis(N,N-diisobutylamido) dichloro neodymate];
sodium [bis(N,N-diisobutylamido) dibromo neodymate];
sodium [bis(N,N-diisobutylamido) diiodo neodymate];
potassium [bis(N,N-diisobutylamido) difluoro neodymate];
potassium [bis(N,N-diisobutylamido) dichloro neodymate];
potassium [bis(N,N-diisobutylamido) dibromo neodymate];
potassium [bis(N,N-diisobutylamido) diiodo neodymate];
lithium [bis(N,N-dibutylamido) difluoro neodymate];
lithium [bis(N,N-dibutylamido) dichloro neodymate];
lithium [bis(N,N-dibutylamido) dibromo neodymate];
lithium [bis(N,N-dibutylamido) diiodo neodymate];
sodium [bis(N,N-dibutylamido) difluoro neodymate];
sodium [bis(N,N-dibutylamido) dichloro neodymate];
sodium [bis(N,N-dibutylamido) dibromo neodymate];
sodium [bis(N,N-dibutylamido) diiodo neodymate];
potassium [bis(N,N-dibutylamido) difluoro neodymate];
potassium [bis(N,N-dibutylamido) dichloro neodymate];
potassium [bis(N,N-dibutylamido) dibromo neodymate];
potassium [bis(N,N-dibutylamido) diiodo neodymate];
lithium [bis(N-methyl-N-propylamido) difluoro neodymate];
lithium [bis(N-methyl-N-propylamido) dichloro neodymate];
lithium [bis(N-methyl-N-propylamido) dibromo neodymate];
lithium [bis(N-methyl-N-propylamido) diiodo neodymate];
sodium [bis(N-methyl-N-propylamido) difluoro neodymate];
sodium [bis(N-methyl-N-propylamido) dichloro neodymate];
sodium [bis(N-methyl-N-propylamido) dibromo neodymate];
sodium [bis(N-methyl-N-propylamido) diiodo neodymate];
potassium [bis(N-methyl-N-propylamido) difluoro neodymate];
potassium [bis(N-methyl-N-propylamido) dichloro neodymate];
potassium [bis(N-methyl-N-propylamido) dibromo neodymate];
potassium [bis(N-methyl-N-propylamido) diiodo neodymate];
lithium [bis(N-methyl-N-butylamido) difluoro neodymate];
lithium [bis(N-methyl-N-butylamido) dichloro neodymate];
lithium [bis(N-methyl-N-butylamido) dibromo neodymate];
lithium [bis(N-methyl-N-butylamido) diiodo neodymate];
sodium [bis(N-methyl-N-butylamido) difluoro neodymate];
sodium [bis(N-methyl-N-butylamido) dichloro neodymate];
sodium [bis(N-methyl-N-butylamido) dibromo neodymate];
sodium [bis(N-methyl-N-butylamido) diiodo neodymate];
potassium [bis(N-methyl-N-butylamido) difluoro neodymate];
potassium [bis(N-methyl-N-butylamido) dichloro neodymate];
potassium [bis(N-methyl-N-butylamido) dibromo neodymate];
potassium [bis(N-methyl-N-butylamido) diiodo neodymate];
lithium [bis(N-methyl-N-isobutylamido) difluoro neodymate];
lithium [bis(N-methyl-N-isobutylamido) dichloro neodymate];
lithium [bis(N-methyl-N-isobutylamido) dibromo neodymate];
lithium [bis(N-methyl-N-isobutylamido) diiodo neodymate];
sodium [bis(N-methyl-N-isobutylamido) difluoro neodymate];
sodium [bis(N-methyl-N-isobutylamido) dichloro neodymate];
sodium [bis(N-methyl-N-isobutylamido) dibromo neodymate];
sodium [bis(N-methyl-N-isobutylamido) diiodo neodymate];
potassium [bis(N-methyl-N-isobutylamido) difluoro neodymate];
potassium [bis(N-methyl-N-isobutylamido) dichloro neodymate];
potassium [bis(N-methyl-N-isobutylamido) dibromo neodymate];
potassium [bis(N-methyl-N-isobutylamido) diiodo neodymate];
lithium [bis(N-methyl-N-t-butylamido) difluoro neodymate];
lithium [bis(N-methyl-N-t-butylamido) dichloro neodymate];
lithium [bis(N-methyl-N-t-butylamido) dibromo neodymate];
lithium [bis(N-methyl-N-t-butylamido) diiodo neodymate];
sodium [bis(N-methyl-N-t-butylamido) difluoro neodymate];

sodium [bis(N-methyl-N-t-butylamido) dichloro neodymate];
sodium [bis(N-methyl-N-t-butylamido) dibromo neodymate];
sodium [bis(N-methyl-N-t-butylamido) diiodo neodymate];
potassium [bis(N-methyl-N-t-butylamido) difluoro neodymate];
potassium [bis(N-methyl-N-t-butylamido) dichloro neodymate];
potassium [bis(N-methyl-N-t-butylamido) dibromo neodymate];
potassium [bis(N-methyl-N-t-butylamido) diiodo neodymate];
lithium [bis(N-ethyl-N-butylamido) difluoro neodymate];
lithium [bis(N-ethyl-N-butylamido) dichloro neodymate];
lithium [bis(N-ethyl-N-butylamido) dibromo neodymate];
lithium [bis(N-ethyl-N-butylamido) diiodo neodymate];
sodium [bis(N-ethyl-N-butylamido) difluoro neodymate];
sodium [bis(N-ethyl-N-butylamido) dichloro neodymate];
sodium [bis(N-ethyl-N-butylamido) dibromo neodymate];
sodium [bis(N-ethyl-N-butylamido) diiodo neodymate];
potassium [bis(N-ethyl-N-butylamido) difluoro neodymate];
potassium [bis(N-ethyl-N-butylamido) dichloro neodymate];
potassium [bis(N-ethyl-N-butylamido) dibromo neodymate];
potassium [bis(N-ethyl-N-butylamido) diiodo neodymate];
lithium [bis(N-propyl-N-butylamido) difluoro neodymate];
lithium [bis(N-propyl-N-butylamido) dichloro neodymate];
lithium [bis(N-propyl-N-butylamido) dibromo neodymate];
lithium [bis(N-propyl-N-butylamido) diiodo neodymate];
sodium [bis(N-propyl-N-butylamido) difluoro neodymate];
sodium [bis(N-propyl-N-butylamido) dichloro neodymate];
sodium [bis(N-propyl-N-butylamido) dibromo neodymate];
sodium [bis(N-propyl-N-butylamido) diiodo neodymate];
potassium [bis(N-propyl-N-butylamido) difluoro neodymate];
potassium [bis(N-propyl-N-butylamido) dichloro neodymate];
potassium [bis(N-propyl-N-butylamido) dibromo neodymate];
potassium [bis(N-propyl-N-butylamido) diiodo neodymate];
lithium [bis(N,N-dipentylamido) difluoro neodymate];
lithium [bis(N,N-dipentylamido) dichloro neodymate];
lithium [bis(N,N-dipentylamido) dibromo neodymate];
lithium [bis(N,N-dipentylamido) diiodo neodymate];
sodium [bis(N,N-dipentylamido) difluoro neodymate];
sodium [bis(N,N-dipentylamido) dichloro neodymate];
sodium [bis(N,N-dipentylamido) dibromo neodymate];
sodium [bis(N,N-dipentylamido) diiodo neodymate];
potassium [bis(N,N-dipentylamido) difluoro neodymate];
potassium [bis(N,N-dipentylamido) dichloro neodymate];
potassium [bis(N,N-dipentylamido) dibromo neodymate];
potassium [bis(N,N-dipentylamido) diiodo neodymate];
lithium [bis(N,N-dihexylamido) difluoro neodymate];
lithium [bis(N,N-dihexylamido) dichloro neodymate];
lithium [bis(N,N-dihexylamido) dibromo neodymate];
lithium [bis(N,N-dihexylamido) diiodo neodymate];
sodium [bis(N,N-dihexylamido) difluoro neodymate];
sodium [bis(N,N-dihexylamido) dichloro neodymate];
sodium [bis(N,N-dihexylamido) dibromo neodymate];
sodium [bis(N,N-dihexylamido) diiodo neodymate];
potassium [bis(N,N-dihexylamido) difluoro neodymate];
potassium [bis(N,N-dihexylamido) dichloro neodymate];
potassium [bis(N,N-dihexylamido) dibromo neodymate];
potassium [bis(N,N-dihexylamido) diiodo neodymate];
lithium [bis(N,N-dioctylamido) difluoro neodymate];
lithium [bis(N,N-dioctylamido) dichloro neodymate];
lithium [bis(N,N-dioctylamido) dibromo neodymate];
lithium [bis(N,N-dioctylamido) diiodo neodymate];
sodium [bis(N,N-dioctylamido) difluoro neodymate];
sodium [bis(N,N-dioctylamido) dichloro neodymate];
sodium [bis(N,N-dioctylamido) dibromo neodymate];
sodium [bis(N,N-dioctylamido) diiodo neodymate];
potassium [bis(N,N-dioctylamido) difluoro neodymate];
potassium [bis(N,N-dioctylamido) dichloro neodymate];
potassium [bis(N,N-dioctylamido) dibromo neodymate];
potassium [bis(N,N-dioctylamido) diiodo neodymate];
lithium [bis(N,N-didecylamido) difluoro neodymate];
lithium [bis(N,N-didecylamido) dichloro neodymate];
lithium [bis(N,N-didecylamido) dibromo neodymate];
lithium [bis(N,N-didecylamido) diiodo neodymate];
sodium [bis(N,N-didecylamido) difluoro neodymate];
sodium [bis(N,N-didecylamido) dichloro neodymate];
sodium [bis(N,N-didecylamido) dibromo neodymate];
sodium [bis(N,N-didecylamido) diiodo neodymate];
potassium [bis(N,N-didecylamido) difluoro neodymate];
potassium [bis(N,N-didecylamido) dichloro neodymate];
potassium [bis(N,N-didecylamido) dibromo neodymate];
potassium [bis(N,N-didecylamido) diiodo neodymate];
lithium [bis(N-benzyl-N-propylamido) difluoro neodymate];
lithium [bis(N-benzyl-N-propylamido) dichloro neodymate];
lithium [bis(N-benzyl-N-propylamido) dibromo neodymate];
lithium [bis(N-benzyl-N-propylamido) diiodo neodymate];
sodium [bis(N-benzyl-N-propylamido) difluoro neodymate];
sodium [bis(N-benzyl-N-propylamido) dichloro neodymate];
sodium [bis(N-benzyl-N-propylamido) dibromo neodymate];
sodium [bis(N-benzyl-N-propylamido) diiodo neodymate];
potassium [bis(N-benzyl-N-propylamido) difluoro neodymate];
potassium [bis(N-benzyl-N-propylamido) dichloro neodymate];
potassium [bis(N-benzyl-N-propylamido) dibromo neodymate];
potassium [bis(N-benzyl-N-propylamido) diiodo neodymate];
lithium [bis(N-benzyl-N-methylamido) difluoro neodymate];
lithium [bis(N-benzyl-N-methylamido) dichloro neodymate];
lithium [bis(N-benzyl-N-methylamido) dibromo neodymate];
lithium [bis(N-benzyl-N-methylamido) diiodo neodymate];
sodium [bis(N-benzyl-N-methylamido) difluoro neodymate];
sodium [bis(N-benzyl-N-methylamido) dichloro neodymate];
sodium [bis(N-benzyl-N-methylamido) dibromo neodymate];
sodium [bis(N-benzyl-N-methylamido) diiodo neodymate];
potassium [bis(N-benzyl-N-methylamido) difluoro neodymate];
potassium [bis(N-benzyl-N-methylamido) dichloro neodymate];
potassium [bis(N-benzyl-N-methylamido) dibromo neodymate];
potassium [bis(N-benzyl-N-methylamido) diiodo neodymate];
lithium [bis(N-benzyl-N-butylamido) difluoro neodymate];
lithium [bis(N-benzyl-N-butylamido) dichloro neodymate];
lithium [bis(N-benzyl-N-butylamido) dibromo neodymate];

lithium [bis(N-benzyl-N-butylamido) diiodo neodymate];
sodium [bis(N-benzyl-N-butylamido) difluoro neodymate];
sodium [bis(N-benzyl-N-butylamido) dichloro neodymate];
sodium [bis(N-benzyl-N-butylamido) dibromo neodymate];
sodium [bis(N-benzyl-N-butylamido) diiodo neodymate];
potassium [bis(N-benzyl-N-butylamido) difluoro neodymate];
potassium [bis(N-benzyl-N-butylamido) dichloro neodymate];
potassium [bis(N-benzyl-N-butylamido) dibromo neodymate];
potassium [bis(N-benzyl-N-butylamido) diiodo neodymate];
lithium [bis(N-benzyl-N-butylamido) difluoro neodymate];
lithium [bis(N-benzyl-N-butylamido) dichloro neodymate];
lithium [bis(N-benzyl-N-butylamido) dibromo neodymate];
lithium [bis(N-benzyl-N-butylamido) diiodo neodymate];
sodium [bis(N-benzyl-N-butylamido) difluoro neodymate];
sodium [bis(N-benzyl-N-butylamido) dichloro neodymate];
sodium [bis(N-benzyl-N-butylamido) dibromo neodymate];
sodium [bis(N-benzyl-N-butylamido) diiodo neodymate];
potassium [bis(N-benzyl-N-butylamido) difluoro neodymate];
potassium [bis(N-benzyl-N-butylamido) dichloro neodymate];
potassium [bis(N-benzyl-N-butylamido) dibromo neodymate];
potassium [bis(N-benzyl-N-butylamido) diiodo neodymate];
lithium [bis(N-benzyl-N-iso-butylamido) difluoro neodymate];
lithium [bis(N-benzyl-N-iso-butylamido) dichloro neodymate];
lithium [bis(N-benzyl-N-iso-butylamido) dibromo neodymate];
lithium [bis(N-benzyl-N-iso-butylamido) diiodo neodymate];
sodium [bis(N-benzyl-N-iso-butylamido) difluoro neodymate];
sodium [bis(N-benzyl-N-iso-butylamido) dichloro neodymate];
sodium [bis(N-benzyl-N-iso-butylamido) dibromo neodymate];
sodium [bis(N-benzyl-N-iso-butylamido) diiodo neodymate];
potassium [bis(N-benzyl-N-iso-butylamido) difluoro neodymate];
potassium [bis(N-benzyl-N-iso-butylamido) dichloro neodymate];
potassium [bis(N-benzyl-N-iso-butylamido) dibromo neodymate];
potassium [bis(N-benzyl-N-iso-butylamido) diiodo neodymate];
lithium [bis(N-cyclohexyl-N-propylamido) difluoro neodymate];
lithium [bis(N-cyclohexyl-N-propylamido) dichloro neodymate];
lithium [bis(N-cyclohexyl-N-propylamido) dibromo neodymate];
lithium [bis(N-cyclohexyl-N-propylamido) diiodo neodymate];
sodium [bis(N-cyclohexyl-N-propylamido) difluoro neodymate];
sodium [bis(N-cyclohexyl-N-propylamido) dichloro neodymate];
sodium [bis(N-cyclohexyl-N-propylamido) dibromo neodymate];
sodium [bis(N-cyclohexyl-N-propylamido) diiodo neodymate];
potassium [bis(N-cyclohexyl-N-propylamido) difluoro neodymate];
potassium [bis(N-cyclohexyl-N-propylamido) dichloro neodymate];
potassium [bis(N-cyclohexyl-N-propylamido) dibromo neodymate];
potassium [bis(N-cyclohexyl-N-propylamido) diiodo neodymate];
lithium [bis(N-cyclohexyl-N-methylamido) difluoro neodymate];
lithium [bis(N-cyclohexyl-N-methylamido) dichloro neodymate];
lithium [bis(N-cyclohexyl-N-methylamido) dibromo neodymate];
lithium [bis(N-cyclohexyl-N-methylamido) diiodo neodymate];
sodium [bis(N-cyclohexyl-N-methylamido) difluoro neodymate];
sodium [bis(N-cyclohexyl-N-methylamido) dichloro neodymate];
sodium [bis(N-cyclohexyl-N-methylamido) dibromo neodymate];
sodium [bis(N-cyclohexyl-N-methylamido) diiodo neodymate];
potassium [bis(N-cyclohexyl-N-methylamido) difluoro neodymate];
potassium [bis(N-cyclohexyl-N-methylamido) dichloro neodymate];
potassium [bis(N-cyclohexyl-N-methylamido) dibromo neodymate];
potassium [bis(N-cyclohexyl-N-methylamido) diiodo neodymate];
lithium [bis(N-cyclohexyl-N-t-butylamido) difluoro neodymate];
lithium [bis(N-cyclohexyl-N-t-butylamido) dichloro neodymate];
lithium [bis(N-cyclohexyl-N-t-butylamido) dibromo neodymate];
lithium [bis(N-cyclohexyl-N-t-butylamido) diiodo neodymate];
sodium [bis(N-cyclohexyl-N-t-butylamido) difluoro neodymate];
sodium [bis(N-cyclohexyl-N-t-butylamido) dichloro neodymate];
sodium [bis(N-cyclohexyl-N-t-butylamido) dibromo neodymate];
sodium [bis(N-cyclohexyl-N-t-butylamido) diiodo neodymate];
potassium [bis(N-cyclohexyl-N-t-butylamido) difluoro neodymate];
potassium [bis(N-cyclohexyl-N-t-butylamido) dichloro neodymate];
potassium [bis(N-cyclohexyl-N-t-butylamido) dibromo neodymate];
potassium [bis(N-cyclohexyl-N-t-butylamido) diiodo neodymate];
lithium [bis(N-cyclohexyl-N-butylamido) difluoro neodymate];
lithium [bis(N-cyclohexyl-N-butylamido) dichloro neodymate];
lithium [bis(N-cyclohexyl-N-butylamido) dibromo neodymate];
lithium [bis(N-cyclohexyl-N-butylamido) diiodo neodymate];
sodium [bis(N-cyclohexyl-N-butylamido) difluoro neodymate];

sodium [bis(N-cyclohexyl-N-butylamido) dichloro neodymate];
sodium [bis(N-cyclohexyl-N-butylamido) dibromo neodymate];
sodium [bis(N-cyclohexyl-N-butylamido) diiodo neodymate];
potassium [bis(N-cyclohexyl-N-butylamido) difluoro neodymate];
potassium [bis(N-cyclohexyl-N-butylamido) dichloro neodymate];
potassium [bis(N-cyclohexyl-N-butylamido) dibromo neodymate];
potassium [bis(N-cyclohexyl-N-butylamido) diiodo neodymate];
lithium [bis(N-cyclohexyl-N-iso-butylamido) difluoro neodymate];
lithium [bis(N-cyclohexyl-N-iso-butylamido) dichloro neodymate];
lithium [bis(N-cyclohexyl-N-iso-butylamido) dibromo neodymate];
lithium [bis(N-cyclohexyl-N-iso-butylamido) diiodo neodymate];
sodium [bis(N-cyclohexyl-N-iso-butylamido) difluoro neodymate];
sodium [bis(N-cyclohexyl-N-iso-butylamido) dichloro neodymate];
sodium [bis(N-cyclohexyl-N-iso-butylamido) dibromo neodymate];
sodium [bis(N-cyclohexyl-N-iso-butylamido) diiodo neodymate];
potassium [bis(N-cyclohexyl-N-iso-butylamido) difluoro neodymate];
potassium [bis(N-cyclohexyl-N-iso-butylamido) dichloro neodymate];
potassium [bis(N-cyclohexyl-N-iso-butylamido) dibromo neodymate];
potassium [bis(N-cyclohexyl-N-iso-butylamido) diiodo neodymate];
lithium [bis(N,N-diphenylamido) difluoro neodymate];
lithium [bis(N,N-diphenylamido) dichloro neodymate];
lithium [bis(N,N-diphenylamido) dibromo neodymate];
lithium [bis(N,N-diphenylamido) diiodo neodymate];
sodium [bis(N,N-diphenylamido) difluoro neodymate];
sodium [bis(N,N-diphenylamido) dichloro neodymate];
sodium [bis(N,N-diphenylamido) dibromo neodymate];
sodium [bis(N,N-diphenylamido) diiodo neodymate];
potassium [bis(N,N-diphenylamido) difluoro neodymate];
potassium [bis(N,N-diphenylamido) dichloro neodymate];
potassium [bis(N,N-diphenylamido) dibromo neodymate];
potassium [bis(N,N-diphenylamido) diiodo neodymate];
lithium [bis(N-phenyl-N-benzylamido) difluoro neodymate];
lithium [bis(N-phenyl-N-benzylamido) dichloro neodymate];
lithium [bis(N-phenyl-N-benzylamido) dibromo neodymate];
lithium [bis(N-phenyl-N-benzylamido) diiodo neodymate];
sodium [bis(N-phenyl-N-benzylamido) difluoro neodymate];
sodium [bis(N-phenyl-N-benzylamido) dichloro neodymate];
sodium [bis(N-phenyl-N-benzylamido) dibromo neodymate];
sodium [bis(N-phenyl-N-benzylamido) diiodo neodymate];
potassium [bis(N-phenyl-N-benzylamido) difluoro neodymate];
potassium [bis(N-phenyl-N-benzylamido) dichloro neodymate];
potassium [bis(N-phenyl-N-benzylamido) dibromo neodymate];
potassium [bis(N-phenyl-N-benzylamido) diiodo neodymate];
lithium [bis(N-pyrrolylamido) difluoro neodymate];
lithium [bis(N-pyrrolylamido) dichloro neodymate];
lithium [bis(N-pyrrolylamido) dibromo neodymate];
lithium [bis(N-pyrrolylamido) diiodo neodymate];
sodium [bis(N-pyrrolylamido) difluoro neodymate];
sodium [bis(N-pyrrolylamido) dichloro neodymate];
sodium [bis(N-pyrrolylamido) dibromo neodymate];
sodium [bis(N-pyrrolylamido) diiodo neodymate];
potassium [bis(N-pyrrolylamido) difluoro neodymate];
potassium [bis(N-pyrrolylamido) dichloro neodymate];
potassium [bis(N-pyrrolylamido) dibromo neodymate];
potassium [bis(N-pyrrolylamido) diiodo neodymate];
lithium [bis(piperidino) difluoro neodymate];
lithium [bis(piperidino) dichloro neodymate];
lithium [bis(piperidino) dibromo neodymate];
lithium [bis(piperidino) diiodo neodymate];
sodium [bis(piperidino) difluoro neodymate];
sodium [bis(piperidino) dichloro neodymate];
sodium [bis(piperidino) dibromo neodymate];
sodium [bis(piperidino) diiodo neodymate];
potassium [bis(piperidino) difluoro neodymate];
potassium [bis(piperidino) dichloro neodymate];
potassium [bis(piperidino) dibromo neodymate];
potassium [bis(piperidino) diiodo neodymate];
lithium [N,N-bis(trimethylsilyl)amido) difluoro neodymate];
lithium [N,N-bis(trimethylsilyl)amido) dibromo neodymate];
lithium [N,N-bis(trimethylsilyl)amido) dichloro neodymate];
lithium [N,N-bis(trimethylsilyl)amido) diiodo neodymate];
sodium [N,N-bis(trimethylsilyl)amido) difluoro neodymate];
sodium [N,N-bis(trimethylsilyl)amido) dichloro neodymate];
sodium [N,N-bis(trimethylsilyl)amido) dibromo neodymate];
sodium [N,N-bis(trimethylsilyl)amido) diiodo neodymate];
potassium [N,N-bis(trimethylsilyl)amido) difluoro neodymate];
potassium [N,N-bis(trimethylsilyl)amido) dichloro neodymate];
potassium [N,N-bis(trimethylsilyl)amido) dibromo neodymate];
potassium [N,N-bis(trimethylsilyl)amido) diiodo neodymate];
lithium [N,N-bis(dimethyl-tert.butyl-silyl)amido) difluoro neodymate];
lithium [N,N-bis(dimethyl-tert.butyl-silyl)amido) dibromo neodymate];
lithium [N,N-bis(dimethyl-tert.butyl-silyl)amido) dichloro neodymate];
lithium [N,N-bis(dimethyl-tert.butyl-silyl)amido) diiodo neodymate];
sodium [N,N-bis(dimethyl-tert.butyl-silyl)amido) difluoro neodymate];
sodium [N,N-bis(dimethyl-tert.butyl-silyl)amido) dichloro neodymate];
sodium [N,N-bis(dimethyl-tert.butyl-silyl)amido) dibromo neodymate];
sodium [N,N-bis(dimethyl-tert.butyl-silyl)amido) diiodo neodymate];
potassium [N,N-bis(dimethyl-tert.butyl-silyl)amido) difluoro neodymate];

potassium [N,N-bis(dimethyl-tert.butyl-silyl)amido) dichloro neodymate];
potassium [N,N-bis(dimethyl-tert.butyl-silyl)amido) dibromo neodymate];
potassium [N,N-bis(dimethyl-tert.butyl-silyl)amido) diiodo neodymate];
lithium [N,N-bis(dimethyl-benzyl-silyl)amido) difluoro neodymate];
lithium [N,N-bis(dimethyl-benzyl-silyl)amido) dibromo neodymate];
lithium [N,N-bis(dimethyl-benzyl-silyl)amido) dichloro neodymate];
lithium [N,N-bis(dimethyl-benzyl-silyl)amido) diiodo neodymate];
sodium [N,N-bis(dimethyl-benzyl-silyl)amido) difluoro neodymate];
sodium [N,N-bis(dimethyl-benzyl-silyl)amido) dichloro neodymate];
sodium [N,N-bis(dimethyl-benzyl-silyl)amido) dibromo neodymate];
sodium [N,N-bis(dimethyl-benzyl-silyl)amido) diiodo neodymate];
potassium [N,N-bis(dimethyl-benzyl-silyl)amido) difluoro neodymate];
potassium [N,N-bis(dimethyl-benzyl-silyl)amido) dichloro neodymate];
potassium [N,N-bis(dimethyl-benzyl-silyl)amido) dibromo neodymate];
potassium [N,N-bis(dimethyl-benzyl-silyl)amido) diiodo neodymate].

The skilled artisan will recognize that additional members of the foregoing list will include the corresponding Lewis base adducts and Group 1 metal halide adducts thereof.

Exemplary, but non-limiting metal complexes according to the invention include the following neodymium complexes:
Bis(N,N-diisopropylamido)neodymium fluoride;
bis(N,N-diisopropylamido)neodymium chloride;
bis(N,N-diisopropylamido)neodymium bromide;
bis(N,N-diisopropylamido)neodymium iodide;
bis(N,N-dipropylamido)neodymium fluoride;
bis(N,N-dipropylamido)neodymium chloride;
bis(N,N-dipropylamido)neodymium bromide;
bis(N,N-dipropylamido)neodymium iodide;
bis(N,N-diethylamido)neodymium fluoride;
bis(N,N-diethylamido)neodymium chloride;
bis(N,N-diethylamido)neodymium bromide;
bis(N,N-diethylamido)neodymium iodide;
bis(N-ethyl-N-methylamido)neodymium fluoride;
bis(N-ethyl-N-methylamido)neodymium chloride;
bis(N-ethyl-N-methylamido)neodymium bromide;
bis(N-ethyl-N-methylamido)neodymium iodide;
bis(N,N-dimethylamido)neodymium fluoride;
bis(N,N-dimethylamido)neodymium chloride;
bis(N,N-dimethylamido)neodymium bromide;
bis(N,N-dimethylamido)neodymium iodide;
bis(N,N-diisobutylamido)neodymium fluoride;
bis(N,N-diisobutylamido)neodymium chloride;
bis(N,N-diisobutylamido)neodymium bromide;
bis(N,N-diisobutylamido)neodymium iodide;
bis(N,N-dibutylamido)neodymium fluoride;
bis(N,N-dibutylamido)neodymium chloride;
bis(N,N-dibutylamido)neodymium bromide;
bis(N,N-dibutylamido)neodymium iodide;
bis(N-methyl-N-propylamido)neodymium fluoride;
bis(N-methyl-N-propylamido)neodymium chloride;
bis(N-methyl-N-propylamido)neodymium bromide;
bis(N-methyl-N-propylamido)neodymium iodide;
bis(N-methyl-N-butylamido)neodymium fluoride;
bis(N-methyl-N-butylamido)neodymium chloride;
bis(N-methyl-N-butylamido)neodymium bromide;
bis(N-methyl-N-butylamido)neodymium iodide;
bis(N-methyl-N-isobutylamido)neodymium fluoride;
bis(N-methyl-N-isobutylamido)neodymium chloride;
bis(N-methyl-N-isobutylamido)neodymium bromide;
bis(N-methyl-N-isobutylamido)neodymium iodide;
bis(N-methyl-N-t-butylamido)neodymium fluoride;
bis(N-methyl-N-t-butylamido)neodymium chloride;
bis(N-methyl-N-t-butylamido)neodymium bromide;
bis(N-methyl-N-t-butylamido)neodymium iodide;
bis(N-ethyl-N-butylamido)neodymium fluoride;
bis(N-ethyl-N-butylamido)neodymium chloride;
bis(N-ethyl-N-butylamido)neodymium bromide;
bis(N-ethyl-N-butylamido)neodymium iodide;
bis(N-propyl-N-butylamido)neodymium fluoride;
bis(N-propyl-N-butylamido)neodymium chloride;
bis(N-propyl-N-butylamido)neodymium bromide;
bis(N-propyl-N-butylamido)neodymium iodide;
bis(N,N-dipentylamido)neodymium fluoride;
bis(N,N-dipentylamido)neodymium chloride;
bis(N,N-dipentylamido)neodymium bromide;
bis(N,N-dipentylamido)neodymium iodide;
bis(N,N-dihexylamido)neodymium fluoride;
bis(N,N-dihexylamido)neodymium chloride;
bis(N,N-dihexylamido)neodymium bromide;
bis(N,N-dihexylamido)neodymium iodide;
bis(N,N-dioctylamido)neodymium fluoride;
bis(N,N-dioctylamido)neodymium chloride;
bis(N,N-dioctylamido)neodymium bromide;
bis(N,N-dioctylamido)neodymium iodide;
bis(N,N-didecylamido)neodymium fluoride;
bis(N,N-didecylamido)neodymium chloride;
bis(N,N-didecylamido)neodymium bromide;
bis(N,N-didecylamido)neodymium iodide;
bis(N-benzyl-N-propylamido)neodymium fluoride;
bis(N-benzyl-N-propylamido)neodymium chloride;
bis(N-benzyl-N-propylamido)neodymium bromide;
bis(N-benzyl-N-propylamido)neodymium iodide;
bis(N-benzyl-N-methylamido)neodymium fluoride;
bis(N-benzyl-N-methylamido)neodymium chloride;
bis(N-benzyl-N-methylamido)neodymium bromide;
bis(N-benzyl-N-methylamido)neodymium iodide;
bis(N-benzyl-tert.-butylamido)neodymium fluoride;
bis(N-benzyl-tert.-butylamido)neodymium chloride;
bis(N-benzyl-tert.-butylamido)neodymium bromide;
bis(N-benzyl-tert.-butylamido)neodymium iodide;
bis(N-benzyl-N-butylamido)neodymium fluoride;
bis(N-benzyl-N-butylamido)neodymium chloride;
bis(N-benzyl-N-butylamido)neodymium bromide;
bis(N-benzyl-N-butylamido)neodymium iodide;
bis(N-benzyl-N-iso-butylamido)neodymium fluoride;
bis(N-benzyl-N-iso-butylamido)neodymium chloride;
bis(N-benzyl-N-iso-butylamido)neodymium bromide;
bis(N-benzyl-N-iso-butylamido)neodymium iodide;
bis(N-cyclohexyl-N-propylamido)neodymium fluoride;
bis(N-cyclohexyl-N-propylamido)neodymium chloride;
bis(N-cyclohexyl-N-propylamido)neodymium bromide;
bis(N-cyclohexyl-N-propylamido)neodymium iodide;
bis(N-cyclohexyl-N-methylamido)neodymium fluoride;
bis(N-cyclohexyl-N-methylamido)neodymium chloride;
bis(N-cyclohexyl-N-methylamido)neodymium bromide;
bis(N-cyclohexyl-N-methylamido)neodymium iodide;
bis(N-cyclohexyl-N-t-butylamido)neodymium fluoride;
bis(N-cyclohexyl-N-t-butylamido)neodymium chloride;
bis(N-cyclohexyl-N-t-butylamido)neodymium bromide;

bis(N-cyclohexyl-N-t-butylamido)neodymium iodide;
bis(N-cyclohexyl-N-butylamido)neodymium fluoride;
bis(N-cyclohexyl-N-butylamido)neodymium chloride;
bis(N-cyclohexyl-N-butylamido)neodymium bromide;
bis(N-cyclohexyl-N-butylamido)neodymium iodide;
bis(N-cyclohexyl-N-iso-butylamido)neodymium fluoride;
bis(N-cyclohexyl-N-iso-butylamido)neodymium chloride;
bis(N-cyclohexyl-N-iso-butylamido)neodymium bromide;
bis(N-cyclohexyl-N-iso-butylamido)neodymium iodide;
bis(N-phenyl-N-benzylamido)neodymium fluoride;
bis(N-phenyl-N-benzylamido)neodymium chloride;
bis(N-phenyl-N-benzylamido)neodymium bromide;
bis(N-phenyl-N-benzylamido)neodymium iodide;
bis(N-pyrrolylamido)neodymium fluoride;
bis(N-pyrrolylamido)neodymium chloride;
bis(N-pyrrolylamido)neodymium bromide;
bis(N-pyrrolylamido)neodymium iodide;
bis(N-piperidino)neodymium fluoride;
bis(N-piperidino)neodymium chloride;
bis(N-piperidino)neodymium bromide;
bis(N-piperidino)neodymium iodide;
bis(N,N-bis(dimethyl-tert.butyl-silyl)amido)neodymium fluoride;
bis(N,N-bis(dimethyl-tert.butyl-silyl)amido)neodymium chloride;
bis(N,N-bis(dimethyl-tert.butyl-silyl)amido)neodymium bromide;
bis(N,N-bis(dimethyl-tert.butyl-silyl)amido)neodymium iodide;
bis(N,N-bis(dimethyl-benzyl-silyl)amido)neodymium fluoride;
bis(N,N-bis(dimethyl-benzyl-silyl)amido)neodymium chloride;
bis(N,N-bis(dimethyl-benzyl-silyl)amido)neodymium bromide;
bis(N,N-bis(dimethyl-benzyl-silyl)amido)neodymium iodide.

The skilled artisan will recognize that additional members of the foregoing list will include the corresponding Lewis base adducts and Group 1 metal halide adducts thereof.

Especially preferred metal complexes according to the present invention corresponding to one of the formulas VIIIa, VIIb or VIIc (formulas see above) are those wherein $R^1$, $R^2$, $R^3$, $R^4$, $R^5$, $R^6$ are hydrocarbyl, especially alkyl, cyclic alkyl, aryl, alkaryl, more especially methyl, ethyl, 1-methylethyl, 1,1-dimethylethyl, cyclohexyl, phenyl, 2,6-dialkylphenyl, benzyl, trimethylsilyl and hydrocarbylsilyl;

D independently each occurrence is selected from carbon monoxide; is phosphines, $PR^i_3$, and phosphites, $P(OR^i)_3$, wherein $R^i$ independently each occurrence is hydrocarbyl, silyl, especially trimethylphosphine, triethylphosphine, tributylphosphine, triphenylphosphine and 1,2-bis(dimethylphosphino)ethane, 1,2-bis(diphenylphosphino)ethane, bis(diphenylphosphino)methane, 1,3-bis(diphenylphosphino)propane, trimethylphosphite, triethylphosphite, tributylphosphite, triphenylphosphite; thioethers, especially dimethylthioether, methylphenylthioether, diethylthioether; ethers and polyethers, especially tetrahydrofuran (THF), diethylether (Et$_2$O), dioxane, 1,2-dimethoxyethane (DME); amines and polyamines, especially pyridine, bipyridine, pyrrolidine, piperidine, tetramethylethylenediamine (TMEDA) and triethylamine (TEA); olefins, especially ethylene, propylene, butene, hexene, octene, styrene, divinylbenzene; conjugated dienes having from 4 to 40 carbon atoms, especially butadiene, isoprene, 1,3-pentadiene, 2,4-hexadiene; alcohols, especially methanol, ethanol, propanol, butanol; nitriles, especially acetonitrile, acrylonitrile, propanenitrile, benzonitrile; esters, especially methyl acetate, ethyl acetate, butyl acetate, methyl acrylate, methyl methacrylate, methyl benzoate;

$X^1$ independently each occurrence are anionic ligand groups having up to 60 atoms, provided however that in no occurrence is $X^1$ an amide group, a phosphide group, a cyclic, delocalized, aromatic group that is π-bonded to M or a allylic delocalized group that is π-bonded to M; especially $X^1$ groups are fluoride, chloride, bromide or iodide, or a hydrocarbyl group, a hydrocarbylsilyl group, a halo-substituted hydrocarbyl group, or an —OR group, wherein R independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, and preferred groups are fluoride, chloride, bromide or iodide;

$X^2$ independently each occurrence are anionic ligand groups having up to 60 atoms, provided however that in no occurrence is $X^2$ a cyclic, delocalized, aromatic group that is π-bonded to M or a allylic delocalized group that is π-bonded to M; especially $X^2$ groups are a hydrocarbyl group, a hydrocarbylsilyl group, a halo-substituted hydrocarbyl group, a silyl group, or an —OR group, wherein R independently each occurrence is hydrogen or a group having from 1 to 80 atoms not is counting hydrogen, which is hydrocarbyl, hydrocarbylsilyl, halo-substituted hydrocarbyl, hydrocarbyloxy-substituted hydrocarbyl, acyl-substituted hydrocarbyl, arylcarbonyl-substituted hydrocarbyl, hydrocarbylamino-substituted hydrocarbyl, hydrocarbylsilyl-substituted hydrocarbyl, acyl or arylcarbonyl, and preferred groups are alkyl or aryl;

i, ii independently each occurrence are as defined above, or are preferably the numbers 0, 1, 2, or 3; and preferably the sum of i and ii represents one of the numbers 1, 2, 3 or 4 and thus must not be zero (i+ii≠0); and $M^{II}$, T, Y, k, s, p, o, y and t are as previously defined; comprising contacting one equivalent of a compound according to formula VIII (see above) with more than 0.3 and less than 4 equivalents of one of the compounds corresponding to formula IXa, IXb or IXc (see above).

More especially preferred metal complexes according to the present invention correspond to one of the formulae VIId, VIIe or VIIf:

Formula VIId

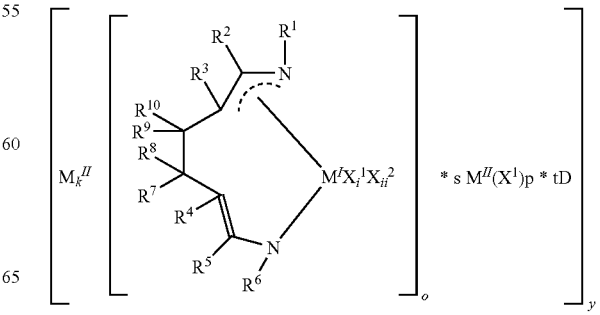

Formula VIIe

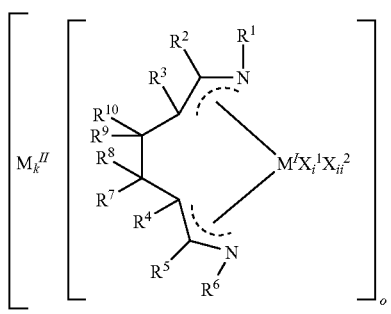

Formula VIIf

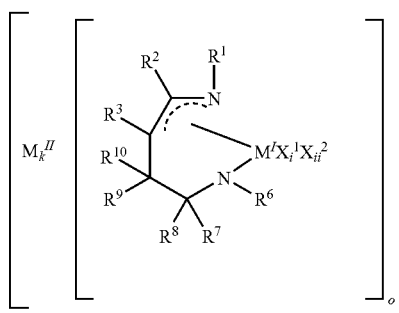

wherein $M^I$, $R^1$, $R^2$, $R^3$, $R^4$, $R^5$, $R^6$, $R^7$, $R^8$, $R^9$, $R^{10}$, $M^{II}$, $X^1$, $X^2$, Y, D, k, s, p, o, y, i, ii, and t are as previously defined; and the formula weight of the metal complex preferably is lower than 10,000 g/mol;

comprising contacting one equivalent of a compound according to the formula VIII (see above) with more than 0.5 and less than 3 equivalents of one of the compounds according to the formulas IXd/e or IXf (see above) in a solvent.

Preferably, $M^I$ comprises a lanthanide metal; even more preferably lanthanum, cerium, praseodymium, neodymium, promethium;

Preferably, $M^{II}$ comprises a lithium, sodium, potassium or magnesium atom; even more preferably lithium, sodium and potassium; and Preferably, D comprises tetrahydrofuran (THF), diethylether (Et2O), dioxane, 1,2-dimethoxyethane (DME).

Even more especially preferred metal complexes according to the present invention are metal complexes corresponding to one of the formulas VIIg, VIIh or VIIi:

Formula VIIg

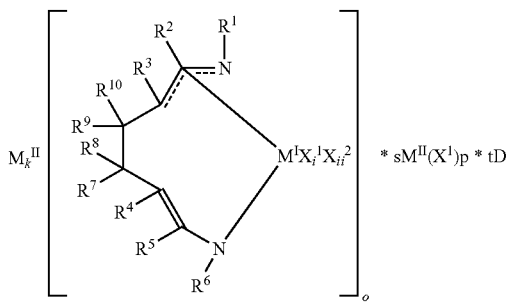

Formula VIIh

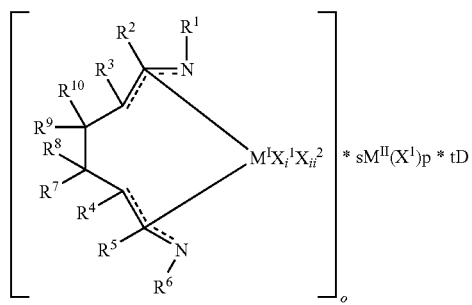

Formula VIIi

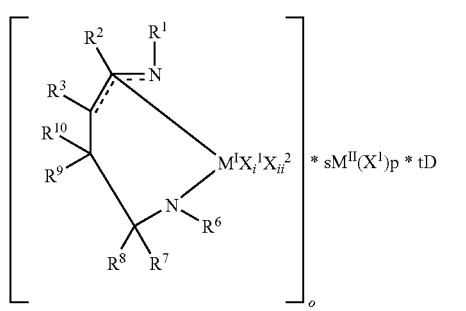

resulting from the reaction of one equivalent of a lanthanide compound corresponding to formula VIII (see above) with one of the compounds corresponding to formula IXd/e or IXf (see above) wherein $R^1$, $R^2$, $R^3$, $R^4$, $R^5$, $R^6$, $R^7$, $R^8$, $R^9$, $R^{10}$ and $X^2$ are alkyl, cyclic alkyl, aryl, alkaryl, more especially methyl, ethyl, 1-methylethyl, 1,1-dimethylethyl, cyclohexyl, phenyl, 2,6-dialkylphenyl, benzyl, trimethylsilyl and benzyl(dimethyl) silyl, t-butyl(dimethyl)silyl, n-butyl(dimethyl)silyl; and $M^I$ is lanthanum, cerium, praseodymium, neodymium, promethium; preferably $M^I$ is neodymium;

N is nitrogen;

$M^{II}$ is lithium, sodium or potassium;

$X^1$ is fluoride, chloride, bromide or iodide;

$X^2$ is are hydrocarbyl, especially alkyl, cyclic alkyl, aryl, alkaryl, more especially methyl, ethyl, 1-methylethyl, 1,1-dimethylethyl, cyclohexyl, phenyl, 2,6-dialkylphenyl, benzyl, trimethylsilyl and hydrocarbylsilyl D is THF, DME or Et2O;

t is the number 0, 1, 2, 3, 4, 5 or 6;

s is the number 0; 1 or 2;

o is the number 1 or 2;

k is the number 0, 1, 2, 3 or 4;

i, ii are the numbers 0, 1 or 2; and preferably the sum of i and ii represents one of the numbers 1, 2 or 3 and thus may not be zero (i+ii≠0); and the formula weight of the metal complex preferably is lower than 6,000 g/mol.

Preferably the metal complex does not contain hapto 5 bond ligands such as, but not limited to, cyclopentadienyl, indenyl or fluorenyl ligands.

In general, the complexes can be prepared by contacting a Group 3, Group 4 or Group 5 metal, lanthanide or actinide compound corresponding to the formula $M^I(X^1)_3$*t D (formula VIII) with one of the compounds corresponding to formula IX, IXa, IXb, IXc, IXd/e or IXf, or a Lewis base adduct thereof, wherein $M^I$, $M^{II}$, T, $R^1$, $R^2$, $R^3$, $R^5$, $R^6$, $R^7$, $R^8$, $R^9$, $R^{10}$, Y, P, D, X, $X^1$, $X^2$, n, m, i, ii, s, p, o, y, k and t are as previously defined; and the molar ratio of the Group 3, Group 4 or Group 5 metal, lanthanide or actinide compound (formula VIII) to the compound corresponding to one of the formula IX, IXa, IXb, IXc, IXd/e or IXf being from 1:0.1 to 1:5.0, preferably from 1:0.3 to 1:3.0, more preferably from 1:0.5 to 1:2.7 and most preferably from 1:0.8 to 1:2.5; in a suitable noninterferring solvent or reaction medium at a temperature from −100° C. to 300° C., preferably from −78° C. to 150° C., most preferably from −20° C. to is 125° C.

By noninterferring is meant that the solvent does not prevent formation of metal complex according to formula VII, VIIa, VIIb, VIIc, VIId, VIIe, VIIf, VIIg, VIIh or VIIi. Suitable reaction media for the formation of the complexes are aliphatic and aromatic hydrocarbons and halohydrocarbons, ethers, amines, alcohols, amides, nitriles and esters. Examples include straight and branched-chain hydrocarbons such as isobutane, butane, pentane, hexane, heptane, octane, and mixtures thereof, cyclic and alicyclic hydrocarbons such as cyclohexane, cycloheptane, methylcyclohexane, methylcycloheptane, and mixtures thereof; chlorinated-, fluorinated- or chlorofluorinated hydrocarbons such as chloroform, dichloromethane, chlorobenzene, dichlorobenzene, and perfluorinated $C_{4-10}$ alkanes; aromatic and hydrocarbyl-substituted aromatic compounds such as benzene, toluene, xylene, and styrene; alkyl ethers having from 1 to 4 carbons in each alkyl group such as diethyl ether, THF and dioxane; $C_{1-4}$ dialkyl ether derivatives of (poly)alkylene glycols, such as DME; aromatic or aliphatic amines such as tetramethylethylenediamine (TMEDA) and triethylamine (TEA); dimethylformamide (DMF) and dimethylacetamide (DMA); nitriles, especially acetonitrile, propanenitrile, benzonitrile; esters, especially methyl acetate, ethyl acetate and butyl acetate. Mixtures of the foregoing are also suitable. Preferred solvents include diethylether, toluene, DME and THF.

The recovery procedure usually involves a separation of the product from the reaction medium and/or any possible byproducts and/or unreacted starting materials. The solvents and other volatile components are advantageously removed via devolatilization of the reaction medium. Extraction into a secondary solvent may be employed if desired. If extraction is employed unpolar aliphatic, aromatic or chlorinated solvents can be used such as but not limited to pentane, hexane, octane, cyclohexane, benzene, toluene, chloroform or dichloromethane and mixtures thereof. Alternatively, if the desired product is an insoluble precipitate, filtration or other separation technique may be employed.

Exemplary, but non-limiting, examples for Group 3 metal, lanthanide or actinide compound according to formula VIII according to the invention include the following neodymium compounds: Neodymium tribromide; neodymium trichloride; neodymium triiodide; neodymium trifluoride, neodymium chloride dibromide; neodymium bromide dichloride; neodymium fluoride dibromide; neodymium bromide difluoride; neodymium fluoride dichloride; and neodymium chloride difluoride.

The skilled artisan will recognize that additional members of the foregoing list will include the corresponding Lewis base adducts thereof.

In general, the complexes described above can be prepared by contacting a Group 3 metal, lanthanide or actinide compound corresponding to Formula II (see above) with Group 1 or 2 compound(s), or a Lewis base adduct thereof, corresponding to Formula IIIa or IIIb (see above), the molar ratio of the Group 3 metal, lanthanide or actinide compound (Formula II) to the Group 1 compound (Formula IIIa or IIIb) being from 1:0.1 to 1:2.8, preferably from 1:0.5 to 1:2.5, more preferably from 1:1.1 to 1:2.5 and most preferably from 1:1.5 to 1:2.5; and the molar ratio of the Group 3 metal, lanthanide or actinide compound (Formula II) to the Group 2 compound (Formula IIIa or IIIb) being from 1:0.05 to 1:1.4, preferably from 1:0.25 to 1:1.25, more preferably from 1:0.6 to 1:1.25 and most preferably from 1:0.75 to 1:1.25, in a suitable noninterfering solvent or reaction medium at a temperature from −100° C. to 300° C., preferably from −78° C. to 150° C., most preferably from 0° C. to 125° C.

By noninterfering is meant that the solvent does not prevent formation of the metal complex according to Formulae Ia, Ib, IVa, IVb, Va, Vb, VIa or VIb. Suitable reaction media for the formation of the complexes are aliphatic and aromatic hydrocarbons and halohydrocarbons, ethers, amines, alcohols, amides, nitriles and esters. Examples include straight and branched-chain hydrocarbons such as isobutane, butane, pentane, hexane, heptane, octane, and mixtures thereof, cyclic and alicyclic hydrocarbons such as cyclohexane, cycloheptane, methylcyclohexane, methylcycloheptane, and mixtures thereof; chlorinated-, fluorinated- or chlorofluorinated hydrocarbons such as chloroform, dichloromethane, chlorobenzene, dichlorobenzene, and perfluorinated $C_{4-10}$ alkanes; aromatic and hydrocarbyl-substituted aromatic compounds such as benzene, toluene, xylene, and styrene; alkyl ethers having from 1 to 4 carbons in each alkyl group such as diethyl ether, THF and dioxane; $C_{1-4}$ dialkyl ether derivatives of (poly)alkylene glycols, such as DME; aromatic or aliphatic amines such as tetramethylethylenediamine (TMEDA) and triethylamine (TEA); dimethylformamide (DMF) and dimethylacetamide (DMA); nitriles, especially acetonitrile, propanenitrile, benzonitrile; esters, especially methyl acetate, ethyl acetate and butyl acetate. Mixtures of the foregoing are also suitable. Preferred solvents include diethylether, toluene, DME and THF.

The recovery procedure usually involves a separation of the product from the reaction medium and/or any possible byproducts and/or unreacted starting materials. The solvents and other volatile components are advantageously removed via devolatilization of the reaction medium. Extraction into a secondary solvent may be employed if desired. If extraction is employed, nonpolar aliphatic, aromatic or chlorinated solvents can be used such as but not limited to pentane, hexane, octane, cyclohexane, benzene, toluene, chloroform or dichloromethane and mixtures thereof. Alternatively, if the desired product is an insoluble precipitate, filtration or other separation technique may be employed.

Exemplary, but non-limiting examples for Group 3 metal, lanthanide or actinide compound according to Formula II according to the invention include the following neodymium compounds: Neodymium tribromide; neodymium trichloride; neodymium triiodide; neodymium trifluoride, neodymium chloride dibromide; neodymium bromide dichloride; neodymium fluoride dibromide; neodymium bromide difluoride; neodymium fluoride dichloride; and neodymium chloride difluoride.

The skilled artisan will recognize that additional members of the foregoing list will include the corresponding Lewis base adducts thereof.

Exemplary, but non-limiting examples for Group 1 or 2 compound(s) according to formula IIIa, IIIb, IIIc or IIId according to the invention include the following compounds:
Lithium [(N,N-diisopropylamide)];
sodium [(N,N-diisopropylamide)];
potassium [(N,N-diisopropylamide)];
magnesium [(N,N-diisopropylamide)];
lithium [(N,N-dipropylamide)];
sodium [(N,N-dipropylamide)];
potassium [(N,N-dipropylamide)];
magnesium [(N,N-dipropylamide)];

lithium [(N,N-diethylamide)];
sodium [(N,N-diethylamide)];
potassium [(N,N-diethylamide)];
magnesium [(N,N-diethylamide)];
lithium [(N-ethyl-N-methylamide)];
sodium [(N-ethyl-N-methylamide)];
potassium [(N-ethyl-N-methylamide)];
magnesium [(N-ethyl-N-methylamide)];
lithium [(N,N-dimethylamide)];
sodium [(N,N-dimethylamide)];
potassium [(N,N-dimethylamide)];
magnesium [(N,N-dimethylamide)];
lithium [(N,N-dimethylamide)];
sodium [(N,N-dimethylamide)];
potassium [(N,N-dimethylamide)];
magnesium [(N,N-dimethylamide)];
lithium [(N,N-diisobutylamide)];
sodium [(N,N-diisobutylamide)];
potassium [(N,N-diisobutylamide)];
magnesium [(N,N-diisobutylamide)];
lithium [(N,N-dibutylamide)];
sodium [(N,N-dibutylamide)];
potassium [(N,N-dibutylamide)];
magnesium [(N,N-dibutylamide)];
lithium [(N-methyl-N-propylamide)];
sodium [(N-methyl-N-propylamide)];
potassium [(N-methyl-N-propylamide)];
magnesium [(N-methyl-N-propylamide)];
lithium [(N-methyl-N-butylamide)];
sodium [(N-methyl-N-butylamide)];
potassium [(N-methyl-N-butylamide)];
magnesium [(N-methyl-N-butylamide)];
lithium [(N-methyl-N-isobutylamide)];
sodium [(N-methyl-N-isobutylamide)];
potassium [(N-methyl-N-isobutylamide)];
magnesium [(N-methyl-N-isobutylamide)];
lithium [(N-methyl-N-tert.-butylamide)];
sodium [(N-methyl-N-tert.-butylamide)];
potassium [(N-methyl-N-tert.-butylamide)];
magnesium [(N-methyl-N-tert.-butylamide)];
lithium [(N-ethyl-N-butylamide)];
sodium [(N-ethyl-N-butylamide)];
potassium [(N-ethyl-N-butylamide)];
magnesium [(N-ethyl-N-butylamide)];
lithium [(N-propyl-N-butylamide)];
sodium [(N-propyl-N-butylamide)];
potassium [(N-propyl-N-butylamide)];
magnesium [(N-propyl-N-butylamide)];
lithium [(N,N-dipentylamide)];
sodium [(N,N-dipentylamide)];
potassium [(N,N-dipentylamide)];
magnesium [(N,N-dipentylamide)];
lithium [(N,N-dihexylamide)];
sodium [(N,N-dihexylamide)];
potassium [(N,N-dihexylamide)];
magnesium [(N,N-dihexylamide)];
lithium [(N,N-dioctylamide)];
sodium [(N,N-dioctylamide)];
potassium [(N,N-dioctylamide)];
magnesium [(N,N-dioctylamide)];
lithium [(N,N-didecylamide)];
sodium [(N,N-didecylamide)];
potassium [(N,N-didecylamide)];
magnesium [(N,N-didecylamide)];
lithium [(N-benzyl-N-propylamide)];
sodium [(N-benzyl-N-propylamide)];
potassium [(N-benzyl-N-propylamide)];
magnesium [(N-benzyl-N-propylamide)];
lithium [(N-benzyl-N-methylamide)];
sodium [(N-benzyl-N-methylamide)];
potassium [(N-benzyl-N-methylamide)];
magnesium [(N-benzyl-N-methylamide)];
lithium [(N-benzyl-N-butylamide)];
sodium [(N-benzyl-N-butylamide)];
potassium [(N-benzyl-N-butylamide)];
magnesium [(N-benzyl-N-butylamide)];
lithium [(N-benzyl-N-s-butylamide)];
sodium [(N-benzyl-N-s-butylamide)];
potassium [(N-benzyl-N-s-butylamide)];
magnesium [(N-benzyl-N-s-butylamide)];
lithium [(N-benzyl-N-iso-butylamide)];
sodium [(N-benzyl-N-iso-butylamide)];
potassium [(N-benzyl-N-iso-butylamide)];
magnesium [(N-benzyl-N-iso-butylamide)];
lithium [(N-cyclohexyl-N-propylamide)];
sodium [(N-cyclohexyl-N-propylamide)];
potassium [(N-cyclohexyl-N-propylamide)];
magnesium [(N-cyclohexyl-N-propylamide)];
lithium [(N-cyclohexyl-N-methylamide)];
sodium [(N-cyclohexyl-N-methylamide)];
potassium [(N-cyclohexyl-N-methylamide)];
magnesium [(N-cyclohexyl-N-methylamide)];
lithium [(N-cyclohexyl-N-tert.-butylamide)];
sodium [(N-cyclohexyl-N-tert.-butylamide)];
potassium [(N-cyclohexyl-N-tert.-butylamide)];
magnesium [(N-cyclohexyl-N-tert.-butylamide)];
lithium [(N,N-diphenylamide)];
sodium [(N,N-diphenylamide)];
potassium [(N,N-diphenylamide)];
magnesium [(N,N-diphenylamide)];
lithium [(N,N-phenylbenzylamide)];
sodium [(N,N-phenylbenzylamide)];
potassium [(N,N-phenylbenzylamide)];
magnesium [(N,N-phenylbenzylamide)];
lithium [(N-pyrrolylamide)];
sodium [(N-pyrrolylamide)];
potassium [(N-pyrrolylamide)];
magnesium [(N-pyrrolylamide)];
lithium [(N-piperidylamide)];
sodium [(N-piperidylamide)];
potassium [(N-piperidylamide];
magnesium [(N-piperidylamide];
lithium [N,N-bis(trimethylsilyl)amide)];
sodium [N,N-bis(trimethylsilyl)amide)];
potassium [N,N-bis(trimethylsilyl)amide];
magnesium [N,N-bis(trimethylsilyl)amide];
lithium [N,N-bis(dimethyl-tert.butyl-silyl)amide)];
sodium [N,N-bis(dimethyl-tert.butyl-silyl)amide)];
potassium [N,N-bis(dimethyl-tert.butyl-silyl)amide];
magnesium [N,N-bis(dimethyl-tert.butyl-silyl)amide];
lithium [N,N-bis(dimethyl-benzyl-silyl)amide)];
sodium [N,N-bis(dimethyl-benzyl-silyl)amide)];
potassium [N,N-bis(dimethyl-benzyl-silyl)amide].
magnesium [N,N-bis(dimethyl-benzyl-silyl)amide].

The skilled artisan will recognize that additional members of the foregoing list will include the corresponding Lewis base adducts and group 1 metal halide adducts thereof.

The catalyst compositions which are useful in the polymerization of ethylenically unsaturated addition polymerizable monomers or in the copolymerization of ethylenically unsaturated addition polymerizable monomers with at least one different type of ethylenically unsaturated addition polymerizable monomer, preferably catalyst compositions which are useful in the polymerization of conjugated ethylenically unsaturated addition polymerizable monomers or in the copolymerization of conjugated ethylenically unsaturated addition polymerizable monomers with at least one different type of ethylenically unsaturated addition polymerizable monomer, according to the invention comprise 1) a combination of one or more of the above metal complexes and one or more activators (cocatalyst) and optionally a support or 2) the reaction product formed by contacting one or more of the above metal complexes with one or more activators and optionally a support or 3) the product formed by subjecting one or more of the above mentioned metal complexes and optionally a support to activating techniques.

The catalyst compositions are formed by rendering the metal complexes catalytically active in a process 1) contacting one or more of the above metal complexes with one or more activators and optionally a support or 2) by subjecting one or more of the above metal complexes to activating techniques optionally in the presence of a support.

The process for the activation of the metal complexes with an activator or cocatalyst or by an activating technique can be performed during a separate reaction step optionally including an isolation of the activated compound or preferably can be performed in situ in the polymerization reactor or just prior to it in an aging reactor, for example. The activation is preferably performed in situ if, after the activation of the metal complex, separation and/or purification of the activated complex is not necessary. The process for the activation of the metal complexes is carried out in a suitable noninterfering solvent or reaction medium at a temperature from −78° C. to 250° C., preferably from −5° C. to 160° C., more preferably from 10° C. to 110° C. Suitable reaction media for the formation of the catalysts compositions are aliphatic and aromatic hydrocarbons and halohydrocarbons. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; chlorinated-, fluorinated- or chlorofluorinated hydrocarbons such as chloroform, dichloromethane, chlorobenzene, dichlorobenzene, and perfluorinated $C_{4-10}$ alkanes; aromatic and hydrocarbyl-substituted aromatic compounds such as benzene, toluene, xylene, and styrene. Advantageously, the reaction medium used for the activation is the same reaction medium as is used in the subsequent polymerization, obviating the need to use a secondary solvent system. In addition to the reaction media mentioned above, this includes heptane or mineral oil fractions such as light or regular petrol, naphtha, kerosine or gas oil and other low-priced aliphatic hydrocarbons or mixtures thereof, as marketed by the petrochemical industry as solvent. An advantage of the invention is that the metal complex catalyst precursors according to the invention can be stored at room temperature or even at elevated temperatures such as, for example, but not limited to, 50° C., in the solid state for extended periods of time. In addition, solutions of the catalyst in suitable solvents also can be stored at room temperature at least for hours. This greatly increases the flexibility of production in an industrial plant. A further advantage of the invention is that the catalysts of the invention usually do not require a separate aging step (see Run 1-11, 13, 16, 18) and if it is desirable to employ an optional aging step, it advantageously does not require long aging times (see Run 12, 17). Therefore, it is possible to start the polymerization reaction just by adding the catalyst components in the desired order into the polymerization reactor. The polymerization can be started for example either by addition of the metal complex as the last component (see for example Runs 2, 3 and 5) or by the addition of the conjugated diene as the last component. If an optional aging step is incorporated into the catalyst preparation/polymerization procedure, the aging time is short, such as less than 60 minutes, preferably less than 40 minutes, more preferably less than 30 min, even more preferably less than 10 min, or even shorter than that and can be performed in a broad temperature range, such as, but not limited to, 0° C. to 150° C. with high catalyst activity. The temperature ranges of the catalyst preparation, catalyst aging and polymerization are independently selected and are between −50° C. and +250° C., preferably between −5 and +160° C., more preferably between 10° C. and 110° C. For example, the catalyst activity of polymerization Run 8 (polymerization temperature 70° C.), amounts to 17.0 kg of polybutadiene per mmol neodymium per hour depending on the polymer conversion ([kg {polymer}/mmol {Nd}[hr]]. In another example, the catalyst activity of polymerization Run 17 (polymerization temperature 80° C.), amounts to 529.1 g of polybutadiene per mmol neodymium per hour ([kg {polymer}/mmol {Nd}[hr]]). It is beneficial that the polymerization reaction can be induced without substantial waiting period (delay) upon addition of the last catalyst component into the polymerization reactor.

Suitable activating cocatalysts for use herein include:

1) neutral Lewis acids, especially a) organo Group 13 compounds, especially i) $C_{1-30}$ organoboron or organoaluminum compounds more especially (hydrocarbyl)aluminum- or (hydrocarbyl)boron compounds, even more especially triaryl and trialkyl aluminum compounds, such as triethyl aluminum, triisobutyl aluminum, trioctylaluminum; alkyl aluminum hydrides, such as diisobutylaluminum hydride; alkylalkoxy aluminum compounds, such as dibutylethoxyaluminum; halogenated aluminum compounds, such as diethylaluminum chloride, ethylaluminum dichloride, diisobutylaluminum chloride, ethyl (octyl)aluminum chloride, ethylaluminum sesquichloride, ethyl(cyclohexyl)aluminum chloride, dicyclohexylaluminum chloride, dioctylaluminum chloride, and ii) organohalogenated (including perhalogenated) derivatives of organo Group 13 compounds, especially halogenated $C_{1-30}$ organoboron or organoaluminum compounds, more especially halogenated (hydrocarbyl)aluminum- or (hydrocarbyl) boron compounds, more especially fluorinated or perfluorinated tri(aryl)boron or -aluminum compounds, such as tris (pentafluorophenyl)boron, tris(pentafluorophenyl) aluminum, tris(o-nonafluorobiphenyl)boron, tris(o-nonafluorobiphenyl)aluminum, tris[3,5-bis(trifluoromethyl) phenyl]boron, tris[3,5-bis(trifluoromethyl)phenyl] aluminum; or b) polymeric or oligomeric alumoxanes, especially methylalumoxane (MAO), triisobutyl aluminum-modified methylalumoxane (MMAO), or isobutylalumoxane; or 2) nonpolymeric, compatible, noncoordinating, ion-forming compounds (including the use of such compounds under oxidizing conditions), especially the use of ammonium-, phosphonium-, oxonium-, carbonium-, silylium-, sulfonium-, or ferrocenium-salts of compatible, noncoordinating anions; and combinations of the foregoing activating compounds. The foregoing activating cocatalysts have been previously taught with respect to different metal complexes in the following references: U.S. Pat. Nos. 5,132,380, 5,153, 157, 5,064,802, 5,321,106, 5,721,185, 5,350,723, and WO-97/04234, equivalent to U.S. Ser. No. 08/818,530, filed Mar. 14, 1997.

Suitable activators for use herein include hydrocarbyl sodium, hydrocarbyl lithium, hydrocarbyl zinc, hydrocarbyl magnesium halide, dihydrocarbyl magnesium, especially alkyl sodium, alkyl lithium, alkyl zinc, alkyl magnesium halide, dialkyl magnesium, such as n-octylsodium, butyllithium, neopentyllithium, methyllithium, ethyllithium, phenyllithium, diethylzinc, dibutylzinc, butylmagnesium chloride, ethylmagnesium chloride, octylmagnesium chloride, dibutylmagnesium, dioctylmagnesium, butyl(octyl)magnesium.

Especially desirable activating cocatalysts for use herein are combinations of neutral optional Lewis acids, especially the combination of a trialkyl aluminum compound having from 1 to 4 carbons in each alkyl group with one or more $C_{1-30}$ hydrocarbyl-substituted Group 13 Lewis acid compounds, especially halogenated is tri(hydrocarbyl)boron or -aluminum compounds having from 1 to 20 carbons in each hydrocarbyl group, especially tris(pentafluorophenyl)borane or tris (pentafluorophenyl)alumane, further combinations of such neutral Lewis acid mixtures with a polymeric or oligomeric alumoxane, and combinations of a single neutral Lewis acid, especially tris(pentafluorophenyl)borane or tris(pentafluorophenyl)alumane, with a polymeric or oligomeric alumoxane. A benefit according to the present invention is the discovery that the most efficient catalyst activation using such a combination of tris(pentafluorophenyl)borane/alumoxane mixture occurs at reduced levels of alumoxane. Preferred molar ratios of the metal complex:tris(pentafluorophenylborane:alumoxane are from 1:1:1 to 1:5:5, more preferably from 1:1:1.5 to 1:5:3. The surprising efficient use of lower levels of alumoxane with the present invention allows for the production of diene polymers with high catalytic efficiencies using less of the expensive alumoxane activator. Additionally, polymers with lower levels of aluminum residue, and hence greater clarity, are obtained.

Suitable ion-forming compounds useful as activators in one embodiment of the present invention comprise a cation which is a Brönsted acid capable of donating a proton, and a compatible, noncoordinating or poorly coordinating anion. As used herein, the term "noncoordinating" means an anion or substance which either does not coordinate to the metal containing precursor complex and the catalytic derivative derived therefrom, or which is only weakly coordinated to such complexes thereby remaining sufficiently labile to be displaced by a Lewis base such as olefin monomer in a manner such that the polymerization may proceed. A noncoordinating anion specifically refers to an anion which when functioning as a charge-balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such activators may be represented by the following general formula:

$$(L^*-H)^+_d A^{d-}$$

wherein:
L* is a neutral Lewis base;
$(L^*-H)^+$ is a Brönsted acid;
$A^{d-}$ is a noncoordinating, compatible anion having a charge of d−, and
d is an integer from I to 3.
More preferably $A^{d-}$ corresponds to the formula:

$$[M^*Q_4]^-;$$

wherein:
M* is boron or aluminum in the +3 formal oxidation state; and
Q independently each occurrence is selected from hydride, dialkylamido, halide, hydrocarbyl, halohydrocarbyl, halocarbyl, hydrocarbyloxide, hydrocarbyloxy substituted-hydrocarbyl, organometal substituted-hydrocarbyl, organometalloid substituted-hydrocarbyl, halohydrocarbyloxy, halohydrocarbyloxy substituted hydrocarbyl, halocarbyl-substituted hydrocarbyl, and halo-substituted silylhydrocarbyl radicals (including perhalogenated hydrocarbyl-, perhalogenated hydrocarbyloxy- and perhalogenated silylhydrocarbyl radicals), said Q having up to 20 carbon atoms with the proviso that in not more than one occurrence is Q halide. Examples of suitable hydrocarbyloxide Q groups are disclosed in U.S. Pat. No. 5,296,433.

In a more preferred embodiment, d is one, that is, the counterion has a single negative charge and is A⁻. Activating cocatalysts comprising boron which are particularly useful in the preparation of catalysts of this invention may be represented by the following general formula:

$$(L^*-H)^+(BQ_4)^-;$$

wherein:
$(L^*-H)^+$ is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl or nonafluorobiphenyl group. Preferred $BQ_4^-$ anions are methyltris(pentafluorophenyl)borate, tetrakis(pentafluorophenyl)borate or tetrakis (nonafluorobiphenyl)borate.

Illustrative, but not limiting, examples of boron compounds which may be used as an activating cocatalyst in the preparation of the improved catalysts of this invention are trisubstituted ammonium salts such as: trimethylammonium tetraphenylborate, tri(n-butyl)ammonium tetraphenylborate, methyldioctadecylammonium tetraphenylborate, triethylammonium tetraphenylborate, tripropylammonium tetraphenylborate, tri(n-butyl)ammonium tetraphenylborate, methyltetradecyloctadecylammonium tetraphenylborate, N,N-dimethylanilinium tetraphenylborate, N,N-diethylanilinium tetraphenylborate, N,N,-2,4,6-pentamethylanilinium)tetraphenylborate, N,N-dimethyl anilinium bis(7,8-dicarbundecaborate)cobaltate (III), trimethylammonium tetrakis(pentafluorophenyl)borate, methyldi(tetradecyl)ammonium tetrakis(pentafluorophenyl)borate, methyldi(octadecyl)ammonium tetrakis(pentafluorophenyl)borate, triethylammonium tetrakis(pentafluorophenyl)borate, tripropylammonium tetrakis(pentafluorophenyl)borate, tri(n-butyl) ammonium tetrakis(pentafluorophenyl)borate, tri(sec-butyl)

ammonium tetrakis(pentafluorophenyl)borate, N,N-dimethylanilinium tetrakis(pentafluorophenyl)borate, N,N-diethylanilinium tetrakis(pentafluorophenyl)borate, N,N,2,4,6-pentamethylanilinium)tetrakis(pentafluorophenyl)borate, trimethylammonium tetrakis(2,3,4,6-tetrafluorophenyl)borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, and N,N,2,4,6-pentamethylanilinium)tetrakis-(2,3,4,6-tetrafluorophenyl)borate; dialkyl ammonium salts such as: di(octadecyl)ammonium tetrakis(pentafluorophenyl)borate, di(tetradecyl)ammonium tetrakis(pentafluorophenyl)borate, and dicyclohexylammonium tetrakis(pentafluorophenyl)borate; trisubstituted phosphonium salts such as: triphenylphosphonium tetrakis(pentafluorophenyl)borate, methyldi(octadecyl)phosphonium tetrakis(pentafluorophenyl)borate, and tris(2,6-dimethylphenyl)phosphonium tetrakis(pentafluorophenyl)borate.

Preferred are tetrakis(pentafluorophenyl)borate salts of long chain alkyl mono-di- and trisubstituted ammonium complexes, especially $C_{14}$-$C_{20}$ alkyl ammonium complexes, especially methyldi(octadecyl)ammonium tetrakis (pentafluorophenyl)borate and methyldi(tetradecyl)ammonium tetrakis(pentafluorophenyl)borate, or mixtures including the same. Such mixtures include protonated ammonium cations derived from amines comprising two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Examples of the most highly preferred catalyst activators herein include the foregoing trihydrocarbylammonium-, especially, methylbis(tetradecyl)ammonium- or methylbis(octadecyl)ammonium-salts of: bis(tris(pentafluorophenyl)borane)imidazolide, bis(tris(pentafluorophenyl)borane)-2-undecylimidazolide, bis(tris(pentafluorophenyl)borane)-2-heptadecylimidazolide, bis(tris(pentafluorophenyl)borane)-4,5-bis(undecyl)imidazolide, bis(tris(pentafluorophenyl)borane)-4,5-bis(heptadecyl)imidazolide, bis(tris(pentafluorophenyl)borane)imidazolinide, bis(tris(pentafluorophenyl)borane)-2-undecylimidazolinide, bis(tris(pentafluorophenyl)borane)-2-heptadecylimidazolinide, bis(tris(pentafluorophenyl)borane)-4,5-bis(undecyl)imidazolinide, bis(tris(pentafluorophenyl)borane)-4,5-bis(heptadecyl)imidazolinide, bis(tris(pentafluorophenyl)borane)-5,6-dimethylbenzimidazolide, bis(tris(pentafluorophenyl)borane)-5,6-bis(undecyl)benzimidazolide, bis(tris(pentafluorophenyl)alumane)imidazolide, bis(tris(pentafluorophenyl)alumane)-2-undecylimidazolide, bis(tris(pentafluorophenyl)alumane)-2-heptadecylimidazolide, bis(tris(pentafluorophenyl)alumane)-4,5-bis(undecyl)imidazolide, bis(tris(pentafluorophenyl)alumane)-4,5-bis(heptadecyl)imidazolide, bis(tris(pentafluorophenyl)alumane)imidazolinide, bis(tris(pentafluorophenyl)alumane)-2-undecylimidazolinide, bis(tris(pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis(heptadecyl)imidazolinide, bis(tris(pentafluorophenyl)alumane)-5,6-dimethylbenzimidazolide, and bis(tris(pentafluorophenyl)alumane)-5,6-bis(undecyl)benzimidazolide. The foregoing activating cocatalysts have been previously taught with respect to different metal complexes in the following reference: EP 1 560 752 A1.

Another suitable ammonium salt, especially for use in heterogeneous catalyst systems, is formed upon reaction of an organometal compound, especially a tri($C_{1-6}$ alkyl)aluminum compound with an ammonium salt of a hydroxyaryltris(fluoroaryl)borate compound. The resulting compound is an organometaloxyaryltris(fluoroaryl)borate compound which is generally insoluble in aliphatic liquids. Examples of suitable compounds include the reaction product of a tri($C_{1-6}$ alkyl) aluminum compound with the ammonium salt of hydroxyaryltris(aryl)borate. Suitable hydroxyaryltris(aryl) borates include the ammonium salts, especially the foregoing long chain alkyl ammonium salts of: (4-dimethylaluminumoxyphenyl)tris(pentafluorophenyl)borate, (4-dimethylaluminumoxy-3,5-di(trimethylsilyl)phenyl)tris(pentafluorophenyl)borate, (4-s dimethylaluminumoxy-3,5-di(t-butyl) phenyl)tris(pentafluorophenyl)borate, (4-dimethylaluminumoxybenzyl)tris(pentafluorophenyl)borate, (4-dimethylaluminumoxy-3-methylphenyl)tris(pentafluorophenyl)borate, (4-dimethylaluminumoxy-tetrafluorophenyl)tris(pentafluorophenyl)borate, (5-dimethylaluminumoxy-2-naphthyl)tris(pentafluorophenyl)borate, 4-(4-dimethylaluminumoxyphenyl)phenyltris(pentafluorophenyl)borate, 4-(2-(4-(dimethylaluminumoxyphenyl)propane-2-yl)phenyloxy)tris(pentafluorophenyl)borate, (4-diethylaluminumoxyphenyl)tris(pentafluorophenyl)borate, (4-diethylaluminumoxy-3,5-di(trimethylsilyl)phenyl)tris(pentafluorophenyl)borate, (4-diethylaluminumoxy-3,5-di(t-butyl)phenyl)tris(pentafluorophenyl)borate, (4-diethylaluminumoxybenzyl) tris(pentafluorophenyl)borate, (4-diethylaluminumoxy-3-methylphenyl) tris(pentafluorophenyl)borate, (4-diethylaluminumoxy-tetrafluorophenyl) tris(pentafluorophenyl)borate, (5-diethylaluminumoxy-2-naphthyl) tris(pentafluorophenyl)borate, 4-(4-diethylaluminumoxyphenyl)phenyl tris(pentafluorophenyl)borate, 4-(2-(4-(diethylaluminumoxyphenyl)propane-2-yl)phenyloxy)tris(pentafluorophenyl)borate, (4-diisopropylaluminumoxyphenyl) tris(pentafluorophenyl) borate, (4-diisopropylaluminumoxy-3,5-di(trimethylsilyl) phenyl)tris(pentafluorophenyl)borate, (4-diisopropylaluminumoxy-3,5-di(t-butyl)phenyl)tris(pentafluorophenyl) borate, (4-diisopropylaluminumoxybenzyl) tris (pentafluorophenyl)borate, (4-diisopropylaluminumoxy-3-methylphenyl) tris(pentafluorophenyl)borate, (4-diisopropylaluminumoxy-tetrafluorophenyl) tris(pentafluorophenyl)borate, (5-diisopropylaluminumoxy-2-naphthyl) tris(pentafluorophenyl)borate, 4-(4-diisopropylaluminumoxyphenyl)phenyl tris(pentafluorophenyl)borate, and 4-(2-(4-(diisopropylaluminumoxyphenyl)propane-2-yl)phenyloxy)tris(pentafluorophenyl)borate.

Especially preferred ammonium compounds are methyldi(tetradecyl)ammonium (4-diethylaluminumoxyphenyl) tris (pentafluorophenyl)borate, methyldi(hexadecyl)ammonium (4-diethylaluminumoxyphenyl)tris(pentafluorophenyl)borate, methyldi(octadecyl)ammonium (4-diethylaluminumoxyphenyl)tris(pentafluorophenyl) borate, and mixtures thereof. The foregoing complexes are disclosed in U.S. Pat. Nos. 5,834,393 and 5,783,512.

Another suitable ion-forming, activating cocatalyst comprises a salt of a cationic oxidizing agent and a noncoordinating, compatible anion represented by the formula:

$$(Ox^{e+})_d(A^{d-})_e,$$

wherein
Ox$^{e+}$ is a cationic oxidizing agent having a charge of e+;
d is an integer from 1 to 3;
e is an integer from 1 to 3; and
A$^{d-}$ is as previously defined.

Examples of cationic oxidizing agents include: ferrocenium, hydrocarbyl-substituted ferrocenium, Pb$^{+2}$ or Ag$^+$. Preferred embodiments of A$^{d-}$ are those anions previously defined with respect to the Bronsted acid containing activating cocatalysts, especially tetrakis(pentafluorophenyl)borate.

Another suitable ion-forming, activating cocatalyst comprises a compound which is a salt of a carbenium ion and a noncoordinating, compatible anion represented by the formula

wherein:
@$^+$ is a C$_{1-20}$ carbenium ion; and
A$^-$ is a noncoordinating, compatible anion having a charge of $-1$. A preferred carbenium ion is the trityl cation, especially triphenylmethylium.

Preferred carbenium salt activating cocatalysts are triphenylmethylium tetrakis(pentafluorophenyl)borate, triphenylmethylium tetrakis(nonafluorobiphenyl)borate, tritolylmethylium tetrakis(pentafluorophenyl)borate and ether substituted adducts thereof.

A further suitable ion-forming, activating cocatalyst comprises a compound which is a salt of a silylium ion and a noncoordinating, compatible anion represented by the formula

wherein:
R is C$_{1-10}$ hydrocarbyl; and
A$^-$ is as previously defined.

Preferred silylium salt activating cocatalysts are trimethylsilylium tetrakis(pentafluorophenyl)borate, trimethylsilylium tetrakis(nonafluorobiphenyl)borate, triethylsilylium tetrakis(pentafluorophenyl)borate and other substituted adducts thereof. Silylium salts have been previously generically disclosed in J. Chem. Soc. Chem. Comm., 1993, 383-384, as well as Lambert, J. B., et al., Organometallics, 1994, 13, 2430-2443. The use of the above silylium salts as activating cocatalysts for addition polymerization catalysts is claimed in U.S. Pat. No. 5,625,087.

Certain complexes of alcohols, mercaptans, silanols, and oximes with tris(pentafluorophenyl)borane are also effective catalyst activators and may be used according to the present invention. Such activators are disclosed in U.S. Pat. No. 5,296,433.

The activating cocatalysts may also be used in combination. An especially is preferred combination is a mixture of a tri(hydrocarbyl)aluminum or tri(hydrocarbyl)borane compound having from 1 to 4 carbons in each hydrocarbyl group with an oligomeric or polymeric alumoxane compound.

The molar ratio of catalyst/activator employed preferably ranges from 1:10,000 to 10:1, more preferably from 1:5000 to 10:1, most preferably from 1:2500 to 1:1. Alumoxane, when used by itself as an activating cocatalyst, is preferably employed in large molar ratio, generally at least 50 times the quantity of metal complex on a molar basis. Tris(pentafluorophenyl)borane, where used as an activating cocatalyst, is preferably employed in a molar ratio to the metal complex of from 0.5:1 to 10:1, more preferably from 1:1 to 6:1 most preferably from 1:1 to 5:1. The remaining activating cocatalysts are generally preferably employed in approximately equimolar quantity with the metal complex.

If the above-mentioned ion-forming compound comprising a compatible non-coordinating or poorly coordinating anion is used as the activator, it is preferable for the metal complex according to the invention to be alkylated (that is, one of the X groups of the metal complex is an alkyl or aryl group). Activators comprising boron are preferred. Most preferred are activators comprising tetrakis(pentafluorophenyl)borate, tris(pentafluorophenyl)borane, tris(o-nonafluorobiphenyl)borane, tetrakis(3,5-bis(trifluoromethyl)phenyl)borate, tris(pentafluorophenyl)alumane, tris(o-nonafluorobiphenyl)alumane.

The molar ratio of the activator relative to the metal center in the metal complex in the case an organometallic compound is selected as the activator, usually is in a range of from 1:10 to 10,000:1, more preferably from 1:10 to 5000:1 and most preferably in a range of from 1:1 to 2,500:1. If a compound containing or yielding a non-coordinating or poorly coordinating anion is selected as activator, the molar ratio usually is in a range of from 1:100 to 1,000:1, and preferably is in range of from 1:2 to 250:1.

Especially desirable activating cocatalysts for use herein are combinations of neutral optional Lewis acids, especially the combination of a trialkyl aluminum compound having from 1 to 4 carbons in each alkyl group with one or more C$_{1-30}$ hydrocarbyl-substituted Group 13 Lewis acid compounds, especially halogenated tetrakis(hydrocarbyl)boron or -aluminum compounds having from 1 to 20 carbons in each hydrocarbyl group, especially tetrakis(pentafluorophenyl)borate, tetrakis(3,5-bis(trifluoromethyl)phenyl)borate, further combinations of a single neutral Lewis acid, especially tetrakis(pentafluorophenyl)borate or tetrakis(3,5-bis(trifluoromethyl)phenyl)borate, with a polymeric or oligomeric alumoxane. A benefit according to the present invention is the discovery that the most efficient catalyst activation using such a combination of tetrakis(pentafluorophenyl)borane/alumoxane mixture occurs at reduced levels of alumoxane.

Preferred molar ratios of the metal complex:tetrakis(pentafluorophenylborane:alumoxane from 1:1:1 to 1:5:1.000, more preferably from 1:1:1.5 to 1:5:500. The surprising efficient use of lower levels of alumoxane with the present invention allows for the production of diene polymers with high catalytic efficiencies using less of the expensive alumoxane activator. Additionally, polymers with lower levels of aluminum residue, and hence greater clarity, are obtained. Preferred molar ratios of the metal complex:tetrakis(pentafluorophenylborane:neutral optional Lewis acids especially trialkyl aluminum or dialkyl aluminum hydride compounds are from 1:1:10 to 1:10:1000, more preferably from 1:1:20 to 1:5:500. Also in this case polymers are obtained with lower levels of aluminum residue, and hence greater clarity, are obtained.

Especially desirable activating cocatalysts for use herein are neutral optional Lewis acids, especially the combination of a trihydrocarbonyl aluminum compound, more especially trialkyl aluminum compound having from 1 to 5 carbons in each alkyl group with neutral Lewis acids containing at least one metal halide bond, especially perhalogenated metals or transition metals, especially boron trifluoride, boron trichloride, boron tribromide, aluminum trifluoride, aluminum trichloride, aluminum tribromide, scandium trifluoride, titanium tetrafluoride, further combinations of a single neutral Lewis acid, especially boron trifluoride, boron trichloride, boron tribromide, aluminum trifluoride, aluminum trichloride, aluminum tribromide, scandium trifluoride, titanium tetrafluoride, with a polymeric or oligomeric alumoxane in a molar ratio of the metal complex:metal fluoride:alumoxane from 1:1:1 to 1:5:10.000, more preferably from 1:1:10 to 1:5:5.000; and further combinations of a single neutral Lewis acid, especially boron trifluoride, boron trichloride, boron tribromide, aluminum trifluoride, aluminum trichloride, aluminum tribromide, scandium trifluoride, titanium tetrafluoride, with trialkyl aluminum or dialkyl aluminum hydride compounds in a molar ratio of the metal complex:tetrakis (pentafluorophenylborane:trialkyl aluminum or dialkyl aluminum hydride compound from 1:1:10 to 1:10:1000, more preferably from 1:1:20 to 1:5:500.

In addition to the metal complex according to the invention and the activator, the catalyst composition can also contain a small amount of another organometallic compound that is used as a so-called scavenger agent. The scavenger agent is added to react with or passivate activity-decreasing impurities in the reaction mixture. It may be added at any time, but normally is added to the reaction mixture before addition of the metal complex and the activator (cocatalyst). Usually organoaluminum compounds are used as scavenger agents. Examples of suitable scavengers are trioctylaluminum, triethylaluminum, diethylaluminum chloride, tri-isobutylaluminum, methylalumoxane or MMAO. The metal complex as well as the activator can be present in the catalyst composition as a single component or as a mixture of several components. For instance, a mixture may be desired where there is a need to influence the molecular properties of the polymer, such as molecular weight distribution.

The reaction system optionally contains a solid material, which serves as carrier or support material for the activator component and/or the metal complex. The carrier material can be chosen from one of the following materials: clay, silica, charcoal (activated carbon), graphite, expanded clay, expanded graphite, carbon black, layered silicates, and alumina. Clays and layered silicates include, but are not limited to, magadiite, montmorillonite, hectorite, sepiolite, attapulgite, smectite, and laponite. Supported catalyst systems of the invention may be prepared by several methods. The metal complex and optionally the activator can be combined before the addition of the support material. The mixture may be prepared in conventional solution in a normally liquid alkane or aromatic solvent. The solvent is preferably also suitable for use as a polymerization diluent for the liquid phase polymerization of an olefin monomer. Alternatively, the activator can be placed on the support material followed by the addition of the metal complex or conversely, the metal complex may be applied to the support material followed by the addition of the activator. The supported catalyst maybe prepolymerized. In addition, third components can be added during any stage of the preparation of the supported catalyst. Third components can be defined as compounds containing Lewis acidic or basic functionalities exemplified by, but not limited to, compounds such as N,N-dimethylaniline, tetraethoxysilane, phenyltriethoxysilane, and bis-tert-butylhydroxytoluene (BHT). The catalyst can be supported onto the carrier material is using techniques such as the solid-phase immobilization (SPI) technique described by H. C. L. Abbenhuis in Angew. Chem. Int. Ed. 37 (1998) 356-58 and by M. Buisio et al., in Microporous Mater., 5 (1995) 211 and by J. S. Beck et al., in J. Am. Chem. Soc., 114 (1992) 10834, as well as the pore volume impregnation (PVI) technique (see WO 97/24344). The isolation of the impregnated carrier can be done by filtration or by removing the volatile material present (that is, solvent) under reduced pressure or by heating.

The support, if present, is preferably employed in an amount to provide a weight ratio of catalyst (based on metal): support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In the polymerization process the catalyst is used in a catalytically effective amount, that is, any amount that successfully results in the formation of polymer. Such amounts may be readily determined by routine experimentation by the worker skilled in the art, but typically the molar ratio of catalyst:polymerizable compounds employed is from $10^{-12}$:1 to $10^{-1}$:1, more preferably from $10^{-12}$:1 to $10^{-3}$:1.

The catalysts may be used to homopolymerize or copolymerize ethylenically unsaturated addition polymerizable monomers preferably conjugated ethylenically unsaturated addition polymerizable monomers having from 2 to 100,000 carbon atoms either alone for homopolymers or in combination with a different type of ethylenically unsaturated addition polymerizable monomers for copolymers. Preferred monomers include α-olefins selected from ethene, propene, 1-butene, 1-pentene, 1-hexene, 4-methyl-1-pentene, 1-octene, styrene, alpha methylstyrene, divinyl benzene, acrylonitrile, acrylic acid ester, methylmethacrylate, ethylmethacrylate and n-butylmethacrylate and conjugated dienes chosen from the group comprising internal conjugated olefins, cyclic conjugated olefins and non-cyclic conjugated olefins. Preferred conjugated dienes are 1,3-butadiene, isoprene (2-methyl-1,3-butadiene), 2,3-dimethyl-1,3-butadiene, 1,3-pentadiene, 2,4-hexadiene, 1,3-hexadiene, 1,4-hexadiene, 1,3-heptadiene, 1,3-octadiene, 2-methyl-2,4-pentadiene, cyclopentadiene, 2,4-hexadiene, 1,3-cyclooctadiene. More preferably butadiene, isoprene and/or cyclopentadiene is used as conjugated diene and ethylene, propene and styrene is used as α-olefin.

Especially desirably formed polymers using the catalyst in the polymerization process of the invention are homo-, co- and terpolymers of conjugated dienes, especially butadiene or isoprene, and random or block copolymers of at least one conjugated diene, especially butadiene, with at least one different type of conjugated diene, especially isoprene, or with an α-olefin, especially ethylene, propene and styrene. Especially preferred are homopolymerization of butadiene or isoprene and random or block copolymerization, optionally terpolymerization, of at least one conjugated diene, especially butadiene with at least one different type of conjugated diene, especially isoprene, or with at least one α-olefin, especially styrene. Highly preferred homopolymers comprise butadiene and highly preferred copolymers comprise conjugated dienes chosen from butadiene or isoprene or comprise butadiene and styrene.

In general, the homopolymerization of the conjugated diene or the copolymerization of one type the conjugated diene monomers with a second type of monomer, an α-olefin or a conjugated diene monomer may be accomplished at conditions well known in the prior art for Ziegler-Natta or Kaminsky-Sinn type polymerization reactions, such as temperatures from −50-250° C. The polymerization can be effected at atmospheric pressure, at sub-atmospheric pressure, or at elevated pressures of up to, or even higher than 500 MPa, continuously or discontinuously. Preferably, the homo- or copolymerization is performed at pressures between 0.01 and 500 MPa, most preferably between 0.01 and 10 MPa, in particular between 0.1-2 MPa. Higher pressures can be applied. In such a high-pressure process the metal complex according to the present invention can also be used with good results. Slurry and solution polymerizations normally take place at lower pressures, preferably below 10 MPa. The polymerization can be carried out in the gas phase as well as in a liquid reaction medium. The polymerization is generally conducted under batch, continuous or semicontinuous polymerization conditions. The polymerization process can be conducted as a gas phase polymerization (for example, in a fluidized bed or stirred bed reactor), as a solution polymerization, wherein the homopolymer or copolymer formed is substantially soluble in the reaction mixture, a suspension/slurry polymerization, wherein the polymer formed is substantially insoluble in the reaction medium, as a solid phase powder polymerization or as a so-called bulk polymerization process, in which an excess of monomer to be polymerized is used as the reaction medium.

The catalysts may also be utilized in combination with at least one additional is homogeneous or heterogeneous polymerization catalyst in the same or in separate reactors connected in series or in parallel to prepare polymer blends having desirable properties. An example of such a process is disclosed in WO 94/00500, equivalent to U.S. Ser. No. 07/904,770, as well as U.S. Pat. No. 5,844,045.

The quantity of catalyst to be used generally is such that its concentration in the solvent or dispersion agent amounts to $10^{-8}$-$10^{-3}$ mol/L, preferably $10^{-7}$-$10^{-4}$ mol/L.

Suitable solvents, dispersion agents or diluents for the polymerization or copolymerization process via a solution or slurry process are typically noncoordinating, inert liquids and can be chosen from the group comprising, but not limited to, straight and branched-chain hydrocarbons such as propane, butane, isobutane, pentane, hexane, heptane, octane, cyclic and alicyclic hydrocarbons such as cyclohexane, cycloheptane, methylcyclohexane, methylcycloheptane, aromatic and alkyl-substituted aromatic compounds such as benzene, toluene, and xylene and isomers of the foregoing and mixtures thereof as well as pentamethyl heptane or mineral oil fractions such as light or regular petrol, naphtha, kerosine or gas oil. Fluorinated hydrocarbon fluids such as perfluorinated $C_{4-10}$ alkanes are also suitable. Further suitable solvents include liquid olefins which may act as comonomers in the polymerization process including cyclopentadiene, butadiene isoprene, butene, pentene and hexene and cyclooctadiene, including isomers of the foregoing. Mixtures of the foregoing are also suitable. Aromatic hydrocarbons, for instance benzene and toluene, can also be used. Out of cost considerations it is preferred therefore to use low-priced aliphatic hydrocarbons or mixtures thereof in polymerization processes on a technical scale as marketed by the petrochemical industry as solvent. If an aliphatic hydrocarbon is used as solvent, the solvent may optionally contain minor quantities of aromatic hydrocarbon, for instance toluene. Thus, if for instance methyl aluminoxane (MAO) is used as activator, toluene can be used as solvent for the MAO in order to supply the MAO in dissolved form to the polymerization reactor. Drying or purification of the solvents is desirable if such solvents are used; this can be done without problems by known methods by one skilled in the art.

Preferably the polymerization or copolymerization is conducted under batch, continuous or semicontinuous solution or bulk polymerization conditions in hydrocarbons such as propylene, propane, butane, butene, pentane, hexane, is heptane, cyclohexane, benzene, toluene, including isomers of the foregoing and mixtures thereof at temperatures from −10° C. and 200° C., preferably from 0° to 130° C. The polymerization may be conducted in one or more continuous stirred reactors or fluidized bed, gas phase reactors, connected in series or parallel. Monomer and/or solvent may be added to the reactor as is well known in the art. The catalyst may also be supported and/or prepolymerized prior to use. A continuous process is preferred, in which event advantageously the mixture of reaction components of catalyst, solvent and dienes is substantially supplied continuously or at frequent intervals into the reactor system and is continuously monitored so as to ensure an efficient reaction and the desired product which is continuously removed therefrom. For example, it is well known that many supported coordination catalysts and catalyst systems for polymerization processes are highly sensitive, in varying degrees, to catalyst poisons such as water, oxygen, carbon oxides, acetylenic compounds and sulfur compounds. Introduction of such compounds may result in reactor upset and production of off-grade product. Typically, computer control systems may be used to maintain process variables within acceptable limits, often by measuring polymer variables such as temperature, viscosity, molecular weight, exotherm, flow rates or catalyst productivity. If the polymerization process is carried out under suspension or gas phase polymerization conditions, the temperatures typically are below 150° C.

Utilizing the catalysts of the present invention, high molecular weight polymers are readily attained by use of the present catalysts, even at elevated reactor temperatures. This result is highly desirable because the molecular weight of diene polymers can be readily reduced by the use of hydrogen, di- and trihydrocarbylaluminum compounds (such as but not limited to triisopropylaluminum, diisopropylaluminum hydride, triethylaluminum, trioctylaluminum, diethylaluminum chloride and diisopropylaluminum chloride), 1,5-cyclooctadiene or similar chain transfer agent. In addition high molecular weights can be reduced using aromatic monomers such as but not limited to styrene (see Run 18). In addition, productivity is increased due to improved polymer solubility, decreased solution viscosity, and a higher polymer concentration.

Utilizing the catalysts of the present invention, homopolymers and copolymers having different comonomer incorporation may be readily prepared.

The homopolymers of the invention such as but not limited to polybutadiene, polyisoprene, polystyrene, polyethylene and polypropylene preferably polybutadiene, polyisoprene and polystyrene, even more preferably polybutadiene and polyisoprene and copolymers of the invention such as but not limited to diene-diene, diene-α-olefin or aromatic α-olefin-nonaromatic alpha olefin co- or terpolymers preferably butadiene-isoprene, butadiene-styrene, butadiene-ethylene and butadiene-propene copolymers, more preferably butadiene-isoprene and butadiene-styrene copolymers can be prepared as completely amorphous copolymers or as copolymers comprising more or less expanded crystalline areas.

With the catalyst and polymerization process of the invention, more or less crystalline, amorphous or rubber-like or rubber homopolymers or copolymers can be prepared depending on the monomers used and depending on the monomer ratios used, especially the diene type A:ethylenically unsaturated addition polymerizable monomer type B ratios or the diene type A:diene type B ratios.

Preferably the percentage of one type of monomers in the copolymer, preferably of one type of conjugated diene is higher than 0 and less than 100 percent. The polybutadiene content of the polybutadiene homopolymer or of the diene-diene copolymers preferably comprises high cis-1,4-polybutadiene.

The polymer resulting from the polymerization or copolymerization can be worked up by a method known per se. In general the catalyst is deactivated at some point during the processing of the polymer in a manner known per se, for example, by means of water or an alcohol. Removal of the catalyst residues can mostly be omitted because the quantity of catalyst in the polymer or copolymer, in particular the content of halogen and metal, is very low owing to the use of the catalyst system according to the invention. If desired, however, the level of catalyst residues in the polymer can be reduced in a known manner, for example, by washing. The deactivation step can be followed by a stripping step (removal of organic solvent(s) from the polymer).

The polymerization or copolymerization can also be performed in several steps, in series as well as in parallel. If required, the catalyst composition, temperature, hydrogen concentration, pressure, residence time, etc., may be varied from step to step. In this way it is also possible to obtain products with a wide property distribution, for example, molecular weight distribution. By using the catalysts of the present invention for the polymerization of olefins, polymers may be obtained with molecular weights between 50,000 and 1,500,000 g/mol preferably is between 100,000 and 1,000,000 g/mol and polydispersities (Mw/Mn) of 1.0-50, preferably polydispersities of 1.0-20.

The polymerization or copolymerization of conjugated dienes by an addition polymerization mechanism results in the formation of residual olefinic vinyl, E (entgegen) and Z (zusammen) double bonds. In the case of butadiene, these are designated vinyl (or 1,2-, or 1,2-polybutadiene), trans (or trans-1,4- or trans-1,4-polybutadiene) and cis (or cis-1,4- or cis-1,4-polybutadiene) double bonds. An advantage of the invention is the possibility to prepare high cis content polybutadiene polymers or copolymers. Preferably the fraction of the residual olefinic double bonds in the polymer or copolymer resulting from the polymerization of the conjugated dienes that are Z or cis units ranges from 50-100 percent, even more preferably from 60 to 100 percent, even more preferably from 80-99 percent, yet still more preferably from 90-99 percent, yet still more preferably from 95-99 percent of the total amount of residual olefinic double bonds resulting from the polymerization of the conjugated dienes. Advantageously the conjugated diene polymers having high cis-1,4-content also have a vinyl content (1,2-polybutadiene and/or 1,2- and 3,4-polyisoprene) between 0 and 30 percent, preferably between 0 and 20 percent, more preferably the 1,2-polybutadiene content of the polybutadiene fraction of the homo- or copolymer is between 0 and 10 percent, even more preferably between 0 and 5 percent. Advantageously according to the invention the cis content of polybutadiene can be very high such as for example but not limited to 94.0 percent (see Run 12) or to 97.9 percent (see Run 3).

Formed copolymerization products of one type of conjugated diene monomer with a second ethylenically unsaturated addition polymerizable monomer preferably can be chosen to be a random or block copolymer, even more preferably the copolymer comprises butadiene and styrene (see run 18) or butadiene and isoprene.

Such polymers of the invention are well-suited for use in the modification of plastics, particularly polystyrene in the preparation of HIPS (high impact polystyrene).

The polymerization process of the invention allows the production of tailor-made copolymers. In particular, the choice of the activator and of the metal complex and also the manner of preparation of catalyst, as well as the solvent used for the polymerization reaction (nonaromatic or aromatic), the concentration of the diene monomers and the polymerization temperature enable an adjustment of the polymer microstructure (ratio of cis-, trans- and vinyl content), the polymer viscosity (Mooney viscosity), the molecular weight of the resulting polymer, the molecular weight distribution and the polymerization activity of a given catalyst. Non-limiting examples are the following:

The average molecular weight (Mw) can be as high as 974,000 g/mol when the neodymium complex 1 was combined with modified methylalumoxane (MMAO) (Run1) while a much lower average molecular weight of Mw=394,000 g/mol resulted when metal complex 1 was combined with diisobutylaluminum hydride and boron trifluoride etherate (Run 11) under similar polymerization conditions. The cis content can be as high as 97.9 percent when complex 1 was combined with diisobutylaluminum hydride and isobutylalumoxane (IBAO) in cyclohexane solvent (Run 3) but also may amount to 66.6 percent when complex 1 was combined with triethylaluminum and [CPh$_3$][B(C$_6$F$_5$)$_4$] (Run 10). The molecular weight distribution can be small such as for example but not limited to 2.5, typical for a single site polymerization process (Run 4) but MWD can also be 7.6 (see Run 6).

The Mooney viscosity can be as high as for example but not limited to 38.2 when the lanthanum complex 9 was combined with modified methylalumoxane (MMAO) (Run 17) while a lower Mooney value amounting to 25.8 resulted when neodymium complex 6 was combined with MMAO (Run 13) under similar polymerization conditions. The cis content can be as high as 94.0 percent when complex 5 was combined with (MMAO) but also may amount to 69.5 percent when complex 9 was combined with MMAO (Run 16). The molecular weight distribution (MWD) can be small such as for example but not limited to 2.2 typical for a single site polymerization process (Run 13) but the MWD can also be 4.7 (see Run 12)

Another advantage which was already mentioned before is the possibility to avoid catalyst aging (see above).

Another advantage of the invention for diene polymerization reactions is that the manner of preparation of the catalyst (for example, order of addition of the catalyst components and catalyst aging) can favorably influence the homo- and copolymer properties such as the polymer microstructure and the molecular weight.

The homo- and copolymers of the invention may be used in the production of many useful shapes, molded parts, films, foams, golf balls, tires, hoses, conveyor and other belts, gaskets, seals, shoes and in the modification of plastics, such as the manufacture of high impact polystyrene or impact-modified polypropylene.

EXAMPLES

It is understood that the present invention is operable in the absence of any component which has not been specifically disclosed. The following examples are provided in order to further illustrate the invention and are not to be constructed as limiting. Unless stated to the contrary, all parts and percentages are expressed on a weight basis. The term "overnight", if used, refers to a time of approximately 16-18 hours, "room temperature", if used, refers to a temperature of 20-25° C.

All tests in which organometallic compounds were involved were carried out in an inert nitrogen atmosphere, using standard Schlenk equipment and techniques or in a glovebox. In the following 'THF' stands for tetrahydrofuran, 'Me' stands for 'methyl', 'Et' stands for 'ethyl', 'Bu' stands for 'butyl', 'Ph' stands for 'phenyl', 'MMAO' or 'MMAO-3a' stands for 'modified methyl alumoxane' purchased from AKZO Nobel and TMB stands for trimethoxybenzene. Pressures mentioned are absolute pressures. The polymerizations were performed under exclusion of moisture and oxygen in a nitrogen atmosphere. The products were characterized by means of SEC (size exclusion chromatography), elemental analysis, NMR (Avance 400 device ($^1$H=400 MHz; $^{13}$C=100 MHz) of Bruker Analytic GmbH) and IR (IFS 66 FT-IR spectrometer of Bruker Optics GmbH). The IR samples were prepared using CS$_2$ as swelling agent and using a two or fourfold dissolution. DSC (differential scanning calorimetry) was measured using a DSC 2920 of TA Instruments.

Mn and Mw are molecular weights and were determined by universal calibration of SEC.

The ratio between the 1,4-cis-, 1,4-trans- and 1,2-polydiene content of the butadiene or isoprene polymers was determined by IR and $^{13}$C NMR-spectroscopy. The glass transition temperatures of the polymers were determined by DSC determination.

1. Synthesis of the Transition Metal Complexes

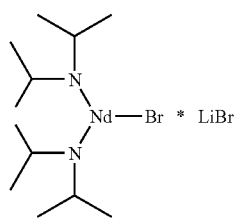

1.1. Preparation of bis(diisopropylamido)neodymium bromide*lithium bromide adduct 1.

In a flask were combined 6.0 g (10 mmol) NdBr$_3$(THF)$_3$ with 200 mL THF at 0° C. About 100 mL of a solution of 1.28 g (20.0 mmol) of lithium diisopropylamide in 100 mL THF were added at 0° C. The mixture was allowed to warm to room temperature and was stirred for an additional 18 hours. The solvent was removed in vacuum and the residue was extracted with pentane. The extracts were centrifuged (or filtered) to remove insoluble material. The clear pentane solution was evaporated to dryness. Yield 87 percent.

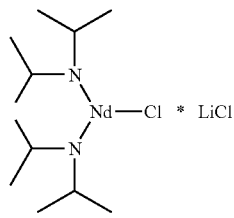

1.2. Preparation of bis(diisopropylamido)neodymium chloride*lithium chloride adduct 2.

In a flask were combined 4.7 g (10 mmol) of NdCl$_3$(THF)$_3$ with 200 mL of THF at 0° C. About 100 mL of a solution of 1.28 g (20.0 mmol) of lithium diisopropylamide in 100 mL of THF were added at 0° C. The mixture was allowed to warm to room temperature and stirred for additional 18 hours. The solvent was removed in vacuum and the residue was extracted with pentane. The extracts were centrifuged (or filtered) to remove insoluble material. The clear pentane solution was evaporated to dryness. Yield 78 percent.

1.3. Preparation of (Et$_2$O)LiN($^i$Pr)—CH=C(Me)—CH(Ph)-CH(Ph)-C(Me)=CH—N($^i$Pr)Li(Et$_2$O) 3

A solution of 20.0 g (106.8 mmol) of the 1-aza-1,3-dienes ($^i$Pr)N=CH—C(Me)=CH(Ph) in 100 mL diethylether were combined with 1.0 g (142.8 mmol) lithium at room is temperature. The mixture was warmed up noticeably upon lithium addition and was stirred for 24 hr's. Subsequently the resulting solution was separated from remaining lithium by filtration and the filtrated solution was evaporated to a volume of 50 mL and stored at −5° C. Crystals of the pale yellow N,N'-dilithium-hexa-1,5-dien-1,6-diamides (Et$_2$O)LiN($^i$Pr)—CH=C(Me)—CH(Ph)-CH(Ph)-C(Me)=CH—N($^i$Pr)Li(Et$_2$O) 3 were formed at this temperature. Yield: 23.0 g (42.7 mmol, 80 percent)

1.4. Preparation of (THF)$_3$LiN[($^i$Pr)$_2$C$_6$H$_3$]—CH=C(Me)-CH(Ph)-CH(Ph)-C(Me)=CH—N[($^i$Pr)$_2$C$_6$H$_3$]Li(THF)$_3$ 4

A solution of 10.0 g (33.0 mmol) of the 1-aza-1,3-PhCH=C(CH$_3$)—CH=N[($^i$Pr)$_2$C$_6$H$_3$] in 100 mL THF were combined with 0.3 g (43.0 mmol) lithium at room temperature and stirred for 48 hr's. Subsequently, the resulting solution was evaporated. The resulting solid residue was extracted with 150 mL diethylether. After filtration of the resulting diethylether solution was stored at 0° C. Crystals of the pale yellow N,N'-dilithium-hexa-1,5-dien-1,6-(THF)$_3$LiN[($^i$Pr)$_2$C$_6$H$_3$]-CH=C(Me)-CH(Ph)-CH(Ph)-C(Me)=CH—N[($^i$Pr)$_2$C$_6$H$_3$]Li(THF)$_3$ 4 were formed at this temperature. Yield: 14.0 g (13.1 mmol, 80 percent)

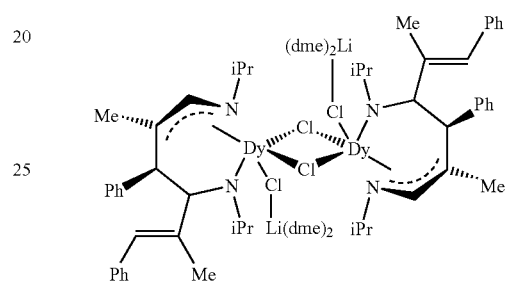

1.5. Preparation of dysprosium complex C$_{68}$H$_{108}$N$_4$O$_8$Cl$_4$Li$_2$Dy$_2$ 5

In a flask were combined 3.40 g (12.65 mmol) DyCl$_3$ with 100 mL dimethoxyethane (dme) at 0° C. The solution was allowed to warm to room temperature and 6.80 g (12.65 mmol) of dilithium(hex-1,5-dien-1,6-diamide)-compound [{Li(OEt$_2$)}$_2${(iPr)NCH=C(Me)CH(Ph)CH(Ph)C(Me)=CHN(iPr)}] 3 were added. The mixture was stirred for additional 24 hours. Precipitated lithium chloride (LiCl) was removed by filtration. The filtrated solution was evaporated to a volume of 50 mL and stored at 0° C. Yellow crystals of the dysprosium compound 5 (M=1590.32 g/mol) were isolated by filtration and dried in the vacuum. yield: 7.47 g (9.40 mmol, 75 percent referred to DyCl$_3$).

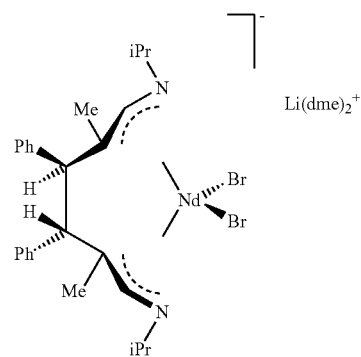

1.6. Preparation of neodymium complex (C$_{38}$H$_{64}$N$_2$O$_6$Br$_2$LiNd) 6.

In a flask were combined 6.80 g (12.65 mmol) of the dilithium(hex-1,5-dien-1,6-diamide)-compound [{Li(OEt$_2$)}$_2${(iPr)NCH=C(Me)CH(Ph)CH(Ph)C(Me)=CHN(iPr)}] 3 in 200 mL dimethoxyethane (dme) with 8.50 g (12.65 mmol) NdBr$_3$(THF)$_4$ at −20° C. The mixture was allowed to warm to room temperature and stirred for 48 hours. Afterwards the reaction solvent was removed in vacuum and the oily residue was extracted with 200 ml diethylether. The solvent was cooled to a temperature of −20° C. At this temperature colorless crystals of LiBr(dme)$_2$ precipitated, which were subsequently removed by filtration. The filtrated solution was evaporated to a volume of 100 mL and stored at room temperature. Slowly neodymium complex 6 crystals were formed. Complex 6 (M=955.9 g) was isolated by filtration and dried in the vacuum. Yield: 2.30 g (2.40 mmol, 19 percent referred to NdBr$_3$(THF)$_4$)

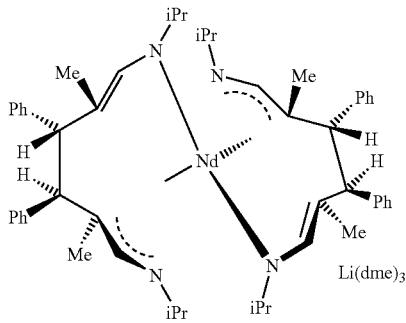

1.7. Preparation of neodymium complex $C_{64}H_{98}N_4O_6LiN$ 7.

In a flask were combined 6.80 g (12.65 mmol) of the dilithium(hex-1,5-dien-1,6-diamide)-compound [{Li(OEt$_2$)}$_2${(iPr)NCH=C(Me)CH(Ph)CH(Ph)C(Me)=CHN(iPr)}] 3 in 150 mL dimethoxyethane (dme) under stirring with 4.25 g (6.30 mmol) NdBr$_3$(THF)$_4$ at −20° C. The mixture was warmed to room temperature and stirred for 24 hours. Afterwards the reaction solvent was removed in vacuum and the residue was extracted with 100 ml diethylether. Precipitated LiBr(dme)$_2$ was removed by is filtration. The filtrated solution was cooled to a temperature of −20° C. and precipitated LiBr(dme)$_2$ was removed by filtration. The filtrated solution was stored at 5° C. whereby neodymium complex 7 crystals were formed. Complex 7 (M=1170.68 g) was isolated by filtration and dried in the vacuum. Yield: 5.50 g (4.73 mmol, 75 percent referred to NdBr$_3$(THF)$_4$).

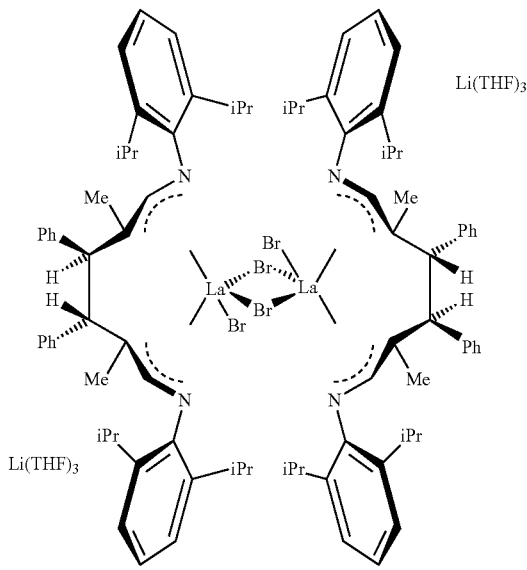

1.8. Preparation of lanthanum complex $C_{108}H_{156}N_4O_6Br_4Li_2La_2$ 8.

In a flask were combined 4.20 g (6.30 mmol) LaBr$_3$(THF)$_4$ in 200 mL tetrahydrofuran (THF) under stirring with 6.61 g (6.25 mmol) of the dilithium(hex-1,5-dien-1,6-diamide)-compound [{Li(THF)$_3$}$_2${(C$_6$H$_3$-2,6-(iPr)$_2$)}NCH=C(Me)CH(Ph)CH(Ph)C(Me)=CHN{C$_6$H$_3$-2,6-(iPr)$_2$}] 4 at −20° C. The mixture was stirred for 48 hours. Afterwards the solvent was evaporated. The residue was solved in 250 mL diethylether and precipitated lithium bromide was removed in the vacuum. The filtrated solution was cooled to a temperature of −20° C. and stored at this temperature for days. Crystals of lanthanum complex 8 were formed. Complex 8 (M=2217.75 g) was isolated by filtration and dried in the vacuum. Yield: 2.80 g (2.52 mmol, 40 percent referred to LaBr$_3$(THF)$_4$).

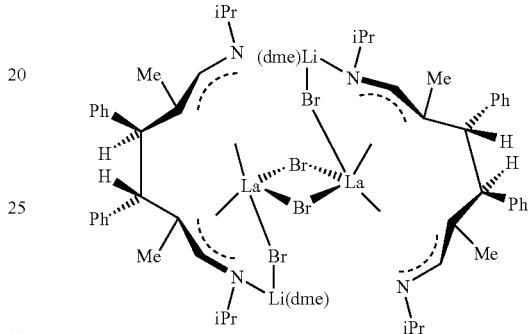

1.9. Preparation of lanthanum complex $C_{60}H_{88}O_4O_4Br_4Li_2La_2$ 9.

In a flask were combined 7.50 g (11.25 mmol) LaBr$_3$(THF)$_4$ in 200 ml dimethoxyethane (dme) under stirring with 6.05 g (11.25 mmol) of the dilithium(hex-1,5-dien-1,6-diamid)-compound [{Li(OEt$_2$)}$_2${(iPr)NCH=C(Me)CH(Ph)CH(Ph)C(Me)=CHN(iPr)}] 3 at a temperature of −20° C. The mixture was stirred for 48 hours. Afterwards the solvent was evaporated. The residue was solved in 200 mL diethylether and precipitated lithium bromide was removed in the vacuum. The filtrated solution was evaporated to a volume of 100 mL and stored at a −20° C. Crystals of lanthanum complex 9 were formed. Complex 9 (M=1540.69 g) was isolated by filtration and dried in the vacuum. Yield: 8.04 g (6.19 mmol, 55 percent referred to LaBr$_3$(THF)$_4$).

2. Polymerization 2.1 Description of the Polymerization Procedure—Method 1

The polymerizations were performed in a double wall 2 L steel reactor, which was purged with nitrogen before the addition of organic solvent, metal complex, activator(s), Lewis acids or other components. The polymerization reactor was is tempered to 70° C. unless stated otherwise. The following components were then added in the following order: organic solvent, the activator 1, conjugated diene monomer(s) and the mixture was allowed to stir for one hour. Then the following components were added in the following order into the 2 L steel reactor: optionally a second activator component and/or Lewis acid and subsequently the metal complex was added to start the polymerization.

The polymerization was performed at 70° C. unless stated otherwise. The polymerization time varied depending on the experiment.

For the termination of the polymerization process, the polymer solution was transferred into a third double wall steel reactor containing 50 mL of methanol and Irganox 1520 as stabilizer for the polymer (1 L of methanol contains 2 g of Irganox). This mixture was stirred for 15 minutes. The recovered polymer was then stripped with steam for 1 hour to remove solvent and other volatiles and dried in an oven at 45° C. for 24 hours.

2.2 Description of the Polymerization Procedure—Method 2

The polymerizations were performed in a double wall 2 L steel reactor, which was purged with nitrogen before the addition of organic solvent, metal complex, activator(s), Lewis acids or other components. The polymerization reactor was tempered to 80° C. if not stated otherwise. The following components were then added in the following order: organic solvent, a portion of the activator 1, conjugated diene monomer(s) and the mixture was allowed to stir for one hour.

In a separate 200 mL double wall steel reactor, which was tempered to the same temperature as the polymerization reactor if the temperature value did not exceed 80° C. (if higher temperatures were chosen for the polymerization process, the 200 mL reactor was still tempered to 80° C.), the following components were added in the following order: organic solvent and a portion of the activator 1 and the mixture was stirred for 0.5 hours. Then optionally a second activator component and/or Lewis acid and subsequently the metal complex were added and the resulting mixture was allowed to stir for an additional 30 minutes.

The polymerization was started through addition of the contents of the 200 mL steel reactor into the 2 L polymerization vessel. The polymerization was performed at a 80° C. unless stated otherwise. The polymerization time varied depending on the experiment.

For the termination of the polymerization process, the polymer solution was transferred into a third double wall steel reactor containing 50 mL of methanol containing Irganox 1520 as stabilizer for the polymer (1 L of methanol contains 2 g of Irganox). This mixture was stirred for 15 minutes. The recovered polymer was then stripped with steam for 1 hour to remove solvent and other volatiles and dried in an oven at 45° C. for 24 hours.

2.3 Description of the Polymerization Procedure—Method 3

The polymerizations were performed in a double wall 2 L steel reactor, which was purged with nitrogen before the addition of organic solvent, metal complex, activator(s), Lewis acids or other components. The polymerization reactor was tempered to 80° C. unless stated otherwise. The following components were then added in the following order: organic solvent, the activator 1, conjugated diene monomer(s) and the mixture was allowed to stir for one hour. Then the following components were added in the following order into the 2 L steel reactor: optionally a second activator component and/or Lewis acid and subsequently the metal complex was added to start the polymerization.

The polymerization was performed at 80° C. unless stated otherwise. The polymerization time varied depending on the experiment.

For the termination of the polymerization process, the polymer solution was transferred into a third double wall steel reactor containing 50 mL of methanol and Irganox 1520 as stabilizer for the polymer (1 L of methanol contains 2 g of Irganox). This mixture was stirred for 15 minutes. The recovered polymer was then stripped with steam for 1 hour to remove solvent and other volatiles and dried in an oven at 45° C. for 24 hours.

3. Polymerization Examples 3.1 Homopolymerization of 1,3-butadiene

A) Polymerization of 1,3-butadiene using complex 1 and MMAO-3a (Run 1)

The experiment was carried out according to the general polymerization procedure described above (2.1). The polymerization was carried out in 540 g of cyclohexane solvent. Thus 540 g of cyclohexane, 54.1 g (1.0 mol) of 1,3-butadiene monomer and MMAO (3.9 g of a heptane solution containing 10.0 mmol of MMAO) were added into the polymerization reactor and stirred for 100 minutes. Afterwards 11.5 mg (0.02 mmol) of neodymium complex 1 dissolved in 3.8 g cyclohexane were added into the polymerization reactor to start the polymerization reaction.

After 10 minutes the polymerization reaction was terminated as described above (see 2.1.). At this point, the conversion level of the monomers into polybutadiene was 73.4 percent. 39.7 g of polybutadiene were recovered as result of the stripping process. The polymer contained 97.3 percent cis-1, 4-; 2.0 percent trans-1,4-, 0.7 percent 1,2-polybutadiene according to IR determination. The molecular weight of the polymer amounted to 974,000 g/mol and the polydispersity (molecular weight distribution) amounted to 2.8. ($M_n$=338,000; $M_z$=1,820,000). The Mooney value amounted to 85.3, the melt enthalpy ($\Delta H^{SL}$) amounts to 43.3 J/g and the glass transition temperature amounted to −107.2° C.

B) Polymerization of 1,3-butadiene using complex 1 IBAO (Run 2)

The experiment was carried out according to the general polymerization procedure described above (2.1). The polymerization was carried out in 542 g of cyclohexane solvent at a polymerization temperature of 80° C. Thus 542 g of cyclohexane, 53.9 g (1.0 mol) of 1,3-butadiene monomer and IBAO (11.2 g of a heptane solution containing 30.0 mmol of IBAO) were added into the polymerization reactor and stirred for 75 minutes. Afterwards 28.6 mg (0.05 mmol) of neodymium complex 1 dissolved in 4.0 g of cyclohexane were added into the polymerization reactor to start the polymerization reaction.

After 44 minutes the polymerization reaction was terminated as described above (see 2.1.). At this point, the conversion level of the monomers into polybutadiene was 43.3 percent. 23.5 g of polybutadiene were recovered as result of the stripping process. The polymer contained 96.5 percent cis-1, 4-; 2.0 percent trans-1,4-, 1.5 percent 1,2-polybutadiene according to IR determination. The Mooney value amounted to 88.1, the melt enthalpy ($\Delta H^{SL}$) amounts to 39.1 J/g and the glass transition temperature amounted to −107.4° C.

C) Polymerization of 1,3-butadiene using complex 1, iBu$_2$AlH and IBAO (Run 3)

The experiment was carried out according to the general polymerization procedure described above (2.1). The polymerization was carried out in 540 g of cyclohexane is solvent at a polymerization temperature of 80° C. Thus 540 g of cyclohexane, 54.3 g (1.0 mol) of 1,3-butadiene monomer, IBAO (5.6 g of a heptane solution containing 15.0 mmol of IBAO) and 270 mg (2 mmol) diisobutylaluminum hydride in 3.7 g of cyclohexane were added into the polymerization reactor and stirred for 80 minutes. Afterwards 14.3 mg (0.025 mmol) of neodymium complex 1 dissolved in 3.5 g of cyclohexane were added into the polymerization reactor to start the polymerization reaction.

After one hour and 17 minutes the polymerization reaction was terminated as described above (see 2.1.). At this point, the conversion level of the monomers into polybutadiene was 70.2 percent. 38.0 g of polybutadiene were recovered as result of the stripping process.

The polymer contained 97.9 percent cis-1,4-; 1.4 percent trans-1,4-, 0.7 percent 1,2-polybutadiene according to IR determination. The molecular weight of the polymer amounted to 566,000 g/mol and the polydispersity (molecular weight distribution) amounted to 3.3. ($M_n$=171,000; $M_z$=1,188,000). The Mooney value amounted to 91.0.

D) Polymerization of 1,3-butadiene using complex 1 and MMAO-3a (Run 4)

The experiment was carried out according to the general polymerization procedure described above (2.1). The polymerization was carried out in 541 g of toluene solvent at a polymerization temperature of 50° C. Thus 541 g of toluene, 54.0 g (1.0 mol) of 1,3-butadiene monomer and MMAO (9.8 g of a heptane solution containing 25.1 mmol of MMAO) were added into the polymerization reactor and stirred for 81 minutes. Afterwards 28.8 mg (0.05 mmol) of neodymium complex 1 dissolved in 3.1 g of toluene were added into the polymerization reactor to start the polymerization reaction.

After two hours and 15 minutes the polymerization reaction was terminated as described above (see 2.1.). At this point, the conversion level of the monomers into polybutadiene was 62.3 percent. 33.7 g of polybutadiene were recovered as result of the stripping process.

The polymer contained 93.0 percent cis-1,4-; 6.1 percent trans-1,4-, 0.9 percent 1,2-polybutadiene according to IR determination. The molecular weight of the polymer amounted to 477,000 g/mol and the polydispersity (molecular weight distribution) amounted to 2.5. ($M_n$=185,000; $M_z$=654,000). The Mooney value amounted to 81.3.

E) Polymerization of 1,3-butadiene using complex 1, $Et_3Al$ and $B(C_6F_5)_3$ (Run 5)

The experiment was carried out according to the general polymerization procedure described above (2.1). The polymerization was carried out in 543 g of cyclohexane solvent. Thus 543 g of cyclohexane, 54.1 g (1.0 mol) of 1,3-butadiene monomer and 0.341 g (3.0 mmol) of triethylaluminum in 1.45 g of cyclohexane were added into the polymerization reactor and stirred for one hour 18 minutes. Afterwards 20.5 mg (0.04 mmol) of tris(pentafluorophenyl)borane dissolved in 3.4 g of cyclohexane solvent and 11.5 mg (0.02 mmol) of neodymium complex 1 dissolved in 3.4 g of cyclohexane were added into the polymerization reactor to start the polymerization reaction. After one hour and 35 minutes the polymerization reaction was terminated as described above (see 2.1.). At this point, the conversion level of the monomers into polybutadiene was 57.3 percent. 31.0 g of polybutadiene were recovered as result of the stripping process.

The polymer contained 92.4 percent cis-1,4-; 6.9 percent trans-1,4-, 0.8 percent 1,2-polybutadiene according to IR determination. The molecular weight of the polymer amounted to 726,000 g/mol and the polydispersity (molecular weight distribution) amounted to 3.1. ($M_n$=233,000; $M_z$=1,730,000). The Mooney value amounted to 112.7.

F) Polymerization of 1,3-butadiene using complex 1, $iBu_2AlH$ and $B(C_6F_5)_3$ (Run 6)

The experiment was carried out according to the general polymerization procedure described above (2.1). The polymerization was carried out in 539 g of cyclohexane solvent. Thus 539 g of cyclohexane and 27 mg (1.5 mmol) of distilled and oxygen-freed (degassed) water were added into the polymerization reactor and stirred for 15 minutes at room temperature. Subsequently 227.3 mg (2.0 mmol) of triethylaluminum, 135 mg (1.0 mg) of diisobutylaluminum hydride and 54.2 g (1.0 mol) of 1,3-butadiene monomer were added into the polymerization reactor and stirred for 1 hour and 18 minutes at 70° C. Afterwards 11.5 mg (0.02 mmol) of neodymium complex 1 dissolved in 3.5 g of cyclohexane were added into the polymerization reactor to start the polymerization reaction.

After two hours the polymerization reaction was terminated as described above (see 2.1.). At this point, the conversion level of the monomers into polybutadiene was 21.6 is percent. 11.7 g of polybutadiene were recovered as result of the stripping process. The polymer contained 95.4 percent cis-1,4-; 3.7 percent trans-1,4-, 0.9 percent 1,2-polybutadiene according to IR determination. The molecular weight of the polymer amounted to 728,000 g/mol and the polydispersity (molecular weight distribution) amounted to 7.6. ($M_n$=96,000; $M_z$=2,050,000).

G) Polymerization of 1,3-butadiene using complex 2, $Et_3Al$ and $B(C_6F_5)_3$ (Run 7)

The experiment was carried out according to the general polymerization procedure described above (2.1). The polymerization was carried out in 540 g of cyclohexane solvent. Thus 540 g of cyclohexane, 54.0 g (1.0 mol) of 1,3-butadiene monomer and 0.341 g (3.0 mmol) of triethylaluminum in 2.4 g of cyclohexane were added into the polymerization reactor and stirred for 28 minutes. Afterwards 20.5 mg (0.04 mmol) of tris(pentafluorophenyl)borane dissolved in 3.2 g of cyclohexane solvent and 9.7 mg (0.02 mmol) of neodymium complex 2 dissolved in 3.6 g of cyclohexane were added into the polymerization reactor to start the polymerization reaction.

After one hour and 30 minutes the polymerization reaction was terminated as described above (see 2.1.). At this point, the conversion level of the monomers into polybutadiene was 55.5 percent. 30.0 g of polybutadiene were recovered as result of the stripping process.

The polymer contained 91.5 percent cis-1,4-; 7.8 percent trans-1,4-, 0.8 percent 1,2-polybutadiene according to IR determination. The molecular weight of the polymer amounted to 486,000 g/mol and the polydispersity (molecular weight distribution) amounted to 3.3. ($M_n$=147,000; $M_z$=1,388,000). The Mooney value amounted to 54.2.

H) Polymerization of 1,3-butadiene using complex 1, $Et_3Al$ and $[C_{18}H_{37})_2NMeH][B(C_6F_5)_4]$ (Run 8)

The experiment was carried out according to the general polymerization procedure described above (2.1). The polymerization was carried out in 542 g of cyclohexane solvent. Thus 542 g of cyclohexane, 53.9 g (1.0 mol) of 1,3-butadiene monomer and 0.341 g (3.0 mmol) of triethylaluminum in 1.83 g of cyclohexane were added into the polymerization reactor and stirred for one hour 41 minutes. Afterwards 36.47 mg (0.03 mmol) of $[C_{18}H_{37})_2NMeH][B(C_6F_5)_4]$ dissolved in 300 mg of methylcyclohexane and 11.5 mg (0.02 mmol) of neodymium complex 1 dissolved in 3.2 g of cyclohexane were added into the polymerization reactor to start the polymerization reaction. After one hour and 8 minutes the polymerization reaction was terminated as described above (see 2.1.). At this point, the conversion level of the monomers into polybutadiene was 83.5 percent. 45.2 g of polybutadiene were recovered as result of the stripping process.

The polymer contained 80.1 percent cis-1,4-; 18.8 percent trans-1,4-, 1.1 percent 1,2-polybutadiene according to IR determination. The Mooney value amounted to 155.3.

I) Polymerization of 1,3-butadiene using complex 1, $iBu_2AlH$ and $[C_{18}H_{37})_2NMeH][B(C_6F_5)_4]$ (Run 9)

The experiment was carried out according to the general polymerization procedure described above (2.1). The polymerization was carried out in 540 g of cyclohexane solvent. Thus 540 g of cyclohexane, 54.2 g (1.0 mol) of 1,3-butadiene monomer and 0.405 g (3.0 mmol) of diisobutylaluminum hydride in 1.5 g of cyclohexane were added into the polymerization reactor and stirred for one hour and 11 minutes. Afterwards 36.47 mg (0.03 mmol) of [$C_{18}H_{37}$)$_2$NMeH][B($C_6F_5$)$_4$] dissolved in 300 mg of methylcyclohexane and 11.5 mg (0.02 mmol) of neodymium complex 1 dissolved in 3.4 g of cyclohexane were added into the polymerization reactor to start the polymerization reaction.

After one hour and 2 minutes the polymerization reaction was terminated as described above (see 2.1.). At this point, the conversion level of the monomers into polybutadiene was 66.8 percent. 36.1 g of polybutadiene were recovered as result of the stripping process.

The polymer contained 83.5 percent cis-1,4-; 15.2 percent trans-1,4-, 1.3 percent 1,2-polybutadiene according to IR determination. The molecular weight of the polymer amounted to 414,000 g/mol and the polydispersity (molecular weight distribution) amounted to 5.8. ($M_n$=71,000; $M_z$=1,200,000). The Mooney value amounted to 87.3.

J) Polymerization of 1,3-butadiene using complex 1, $Et_3Al$ and [$CPh_3$][B($C_6F_5$)$_4$] (Run 10)

The experiment was carried out according to the general polymerization procedure described above (2.1). The polymerization was carried out in 540 g of toluene is solvent. Thus 540 g of toluene, 54.2 g (1.0 mol) of 1,3-butadiene monomer and 0.341 g (3.0 mmol) triethylaluminum in 2.1 g of toluene were added into the polymerization reactor and stirred for one hour. Afterwards 20.1 mg (0.03 mmol) of [$CPh_3$][B($C_6F_5$)$_4$] dissolved in 3.4 g of toluene solvent and 11.5 mg (0.02 mmol) of neodymium complex 1 dissolved in 4.8 g of toluene were added into the polymerization reactor to start the polymerization reaction.

After one hour and 34 minutes the polymerization reaction was terminated as described above (see 2.1.). At this point, the conversion level of the monomers into polybutadiene was 80.6 percent. 43.6 g of polybutadiene were recovered as result of the stripping process.

The polymer contained 66.6 percent cis-1,4-; 31.8 percent trans-1,4-, 1.5 percent 1,2-polybutadiene according to IR determination. The molecular weight of the polymer amounted to 300,000 g/mol and the polydispersity (molecular weight distribution) amounted to 5.0. ($M_n$=60,000; $M_z$=1,900,000). The Mooney value amounted to 23.6.

K) Polymerization of 1,3-butadiene using complex 1, i-$Bu_2AlH$ and $BF_3$ (Run 11)

The experiment was carried out according to the general polymerization procedure described above (2.1). The polymerization was carried out in 541 g of toluene solvent. Thus 541 g of toluene, 54.2 g (1.0 mol) of 1,3-butadiene monomer and 0.405 g (3.0 mmol) of diisopropylaluminum hydride in 3.8 g of toluene were added into the polymerization reactor and stirred for one hour and 45 minutes. Afterwards 6.5 mg (0.046 mmol) of $BF_3*Et_2O$ 0.0046 dissolved in 4.6 g of toluene solvent and 11.5 mg (0.020 mmol) of neodymium complex 1 dissolved in 6.6 g of toluene were added into the polymerization reactor to start the polymerization reaction.

After two hours and 50 minutes the polymerization reaction was terminated as described above (see 2.1.). At this point, the conversion level of the monomers into polybutadiene was 83.7 percent. 45.3 g of polybutadiene were recovered as result of the stripping process.

The polymer contained 86.2 percent cis-1,4-; 12.6 percent trans-1,4-, 1.2 percent 1,2-polybutadiene according to IR determination. The molecular weight of the polymer amounted to 394,000 g/mol and the polydispersity (molecular weight distribution) amounted to 4.0. ($M_n$=98,000; $M_z$=1,530,000). The Mooney value amounted to 30.5.

L) Polymerization of 1,3-butadiene using complex 5 and MMAO-3a (Run 12)

The experiment was carried out according to the general polymerization procedure described above (2.2.). The polymerization was carried out in 508 g of cyclohexane solvent and 70 g of toluene solvent. Thus 508 g of cyclohexane, 55.2 g (1.0 mol) of 1,3-butadiene monomer and MMAO (5.9 g of a heptane solution containing 15.1 mmol of MMAO) were added into the polymerization reactor. 70 g of toluene and 5.9 g of a heptane solution containing 15.0 mmol of MMAO were mixed with 159 mg (0.10 mmol) of the metal complex 5 in a separate reaction vessel and stirred for 30 minutes.

Afterwards the resulting mixture was transferred into the polymerization reactor to start the polymerization reaction.

After one hours and 33 minutes the polymerization reaction was terminated as described above (see 2.2.). At this point, the conversion level of the monomers into polybutadiene was 27.7 percent. 15.3 g of polybutadiene were recovered as result of the stripping process.

The polymer contained 94.0 percent cis-1,4-; 3.0 percent trans-1,4-, 3.0 percent 1,2-polybutadiene according to $^{13}$C-NMR determination The molecular weight of the polymer amounted to 512,000 g/mol and the polydispersity (molecular weight distribution) amounted to 4.74. ($M_n$=108,000; $M_z$=1,430,000).

M) Polymerization of 1,3-butadiene using complex 6 and MMAO-3a (Run 13)

The experiment was carried out according to the general polymerization procedure described above (2.3). The polymerization was carried out in 500 g of cyclohexane solvent. Thus 496.7 g of cyclohexane, 54.1 g (1.0 mol) of 1,3-butadiene monomer and MMAO (11.8 g of a heptane solution containing 30.3 mmol of MMAO) were 11) added into the polymerization reactor and stirred for one hour and 30 minutes. Afterwards 95.6 mg (0.10 mmol) of neodymium complex 6 dissolved in 3.3 g cyclohexane were added into the polymerization reactor to start the polymerization reaction.

After two hours and 16 minutes the polymerization reaction was terminated as is described above (see 2.3.). At this point, the conversion level of the monomers into polybutadiene was 82.1 percent. 44.4 g of polybutadiene were recovered as result of the stripping process.

The polymer contained 93.5 percent cis-1,4-; 5.5 percent trans-1,4-, 1.0 percent 1,2-polybutadiene according to $^{13}$C-NMR determination. The molecular weight of the polymer amounted to 283,500 g/mol and the polydispersity (molecular weight distribution) amounted to 2.23. ($M_n$=127,000; $M_z$=592,000). The Mooney value amounted to 25.8.

N) Polymerization of 1,3-butadiene using complex 7 and MMAO-3a (Run 14)

The experiment was carried out according to the general polymerization procedure described above (2.3). The polymerization was carried out in 500 g of cyclohexane. Thus 495.6 g of cyclohexane, 54.1 g (1.0 mol) of 1,3-butadiene monomer and MMAO (11.6 g of a heptane solution containing 30.0 mmol of MMAO) were added into the polymerization reactor and stirred for one hour and 7 minutes. Afterwards 95.0 mg (0.081 mmol) of neodymium complex 7 dissolved in 4.4 g cyclohexane were added into the polymerization reactor to start the polymerization reaction.

After one hour and 39 minutes the polymerization reaction was terminated as described above (see 2.2.). At this point, the conversion level of the monomers into polybutadiene was 5.1 percent. 2.8 g of polybutadiene were recovered as result of the stripping process.

O) Polymerization of 1,3-butadiene using complex 8 and MMAO-3a (Run 15)

The experiment was carried out according to the general polymerization procedure described above (2.2.). The polymerization was carried out in 500.9 g of cyclohexane. Thus 401.0 g of cyclohexane, 55.1 g (1.0 mol) of 1,3-butadiene monomer and MMAO (6.0 g of a heptane solution containing 15.3 mmol of MMAO) were added into the polymerization reactor. 90.5 g of cyclohexane and 5.9 g of a heptane solution containing 15.2 mmol of MMAO were mixed with 103.7 mg (0.047 mmol) of the metal complex 8 dissolved in 9.4 g cyclohexane in a separate reaction vessel and stirred for one hour and 16 minutes.

Afterwards the resulting mixture was transferred into the polymerization reactor to start the polymerization reaction.

After one hours and 35 minutes the polymerization reaction was terminated as described above (see 2.2.). At this point, the conversion level of the monomers into polybutadiene was 3.5 percent. 1.9 g of polybutadiene were recovered as result of the stripping process.

P) Polymerization of 1,3-butadiene using complex 9 and MMAO-3a (Run 16)

The experiment was carried out according to the general polymerization procedure described above (2.3). The polymerization was carried out in 500 g of cyclohexane. Thus 491.6 g of cyclohexane, 54.1 g (1.0 mol) of 1,3-butadiene monomer and MMAO (11.8 g of a heptane solution containing 30.3 mmol of MMAO) were added into the polymerization reactor and stirred for 34 minutes. Afterwards 82.4 mg (0.053 mmol) of neodymium complex 9 dissolved in 8.4 g cyclohexane were added into the polymerization reactor to start the polymerization reaction.

After one hour and 46 minutes the polymerization reaction was terminated as described above (see 2.3.). At this point, the conversion level of the monomers into polybutadiene was 46.8 percent. 25.3 g of polybutadiene were recovered as result of the stripping process.

The polymer contained 69.5 percent cis-1,4-; 12.5 percent trans-1,4-, 8.5 percent 1,2-polybutadiene according to IR determination. The Mooney value amounted to 33.9.

Q) Polymerization of 1,3-butadiene using complex 9 and MMAO-3a (Run 17)

The experiment was carried out according to the general polymerization procedure described above (2.2.). The polymerization was carried out in 2000.7 g of cyclohexane. Thus 1901 g of cyclohexane, 218.0 g (4.0 mol) of 1,3-butadiene monomer and MMAO (11.9 g of a heptane solution containing 31.0 mmol of MMAO) were added into the polymerization reactor. 91.5 g of cyclohexane and 11.9 g of a heptane solution containing 31.0 mmol of MMAO were mixed with 164.8 mg (0.107 mmol) of the metal complex 9 dissolved in 7.5 g cyclohexane in a separate reaction vessel and stirred for 44 minutes.

Afterwards the resulting mixture was transferred into the polymerization reactor to start the polymerization reaction.

After one hours and 34 minutes the polymerization reaction was terminated as described above (see 2.2.). At this point, the conversion level of the monomers into polybutadiene was 44.5 percent. 97.0 g of polybutadiene were recovered as result of is the stripping process.

The polymer contained 93.7 percent cis-1,4-; 4.7 percent trans-1,4-, 1.7 percent 1,2-polybutadiene according to $^{13}$C-NMR determination. The Mooney value amounted to 38.2.

3.2 Copolymerization of 1,3-butadiene and styrene

R) Copolymerization of 1,3-butadiene and styrene using complex 1 Et$_3$Al and [C$_{18}$H$_{37}$)$_2$NMeH][B(C$_6$F$_5$)$_4$] (Run 18)

The experiment was carried out according to the general polymerization procedure described above (2.1). The polymerization was carried out in 542 g of cyclohexane solvent. Thus 542 g of cyclohexane, 54.1 g (1.0 mol) of 1,3-butadiene monomer, 20.9 g (0.20 mol) of styrene monomer and 0.341 g (3.0 mmol) of triethylaluminum in 1.5 g of cyclohexane were added into the polymerization reactor and stirred for three hours eight minutes. Afterwards 36.47 mg (0.03 mmol) of [C$_{18}$H$_{37}$)$_2$NMeH][B(C$_6$F$_5$)$_4$] (RIBS 2) dissolved in 300 mg of methylcyclohexane and 11.5 mg (0.02 mmol) of neodymium complex 1 dissolved in 4.0 g of cyclohexane were added into the polymerization reactor to start the polymerization reaction.

After three hours and two minutes the polymerization reaction was terminated as described above (see 2.1.). At this point, the conversion level of the monomers into polybutadiene was 27.3 percent. 14.8 g of polybutadiene were recovered as result of the stripping process.

The polymer contained 85.4 percent cis-1,4-; 13.4 percent trans-1,4-, 1.0 percent 1,2-polybutadiene and 0.2 percent styrene according to IR and $^{13}$C-NMR determination. The molecular weight of the polymer amounted to 362,000 g/mol and the polydispersity (molecular weight distribution) amounted to 5.0. ($M_n$=72,000; $M_z$=2,363,000).

| 3.3 Polymerization activity - Comparison | |
|---|---|
| Run | Activity [kg {polymer}/mmol {Nd}[hr]] |
| 1 | 17.01** |
| 2 | 0.58* |
| 3 | 3.08* |
| 4 | 0.52* |
| 5 | 3.47** |
| 6 | 0.82* |
| 7 | 2.07** |
| 8 | 16.95*** |
| 9 | 9.95** |
| 10 | 2.03* |
| 11 | 2.60* |
| 18 | 1.24* |

*measured after 15 minutes;
**measured after 10 minutes;
***measured after 8 minutes

| Run | Activity [g {polymer}/mmol {Nd}[hr]] |
|---|---|
| 12 | 71.6* |
| 13 | 116.4* |
| 14 | 23.3* |
| 15 | 14.2** |
| 16 | 400.1* |
| 17 | 529.1* |

*measured after 30 minutes;
**measured after 60 minutes;

| 3.4 Molecular weight - Comparison | | | | | | | |
|---|---|---|---|---|---|---|---|
| Run | Mw | Mn | Mz | Run | Mw | Mn | Mz |
| 1 | 974,000 | 338,000 | 1,820,000 | 8 | not. det. | not. det. | not. det. |
| 2 | not. det. | not. det. | not. det. | 9 | 414,000 | 71,000 | 1,200,000 |
| 3 | 566,000 | 171,000 | 1,188,000 | 10 | 300,000 | 60,000 | 1,900,000 |
| 4 | 477,000 | 185,000 | 654,000 | 11 | 394,000 | 98,000 | 1,530,000 |
| 5 | 726,000 | 233,000 | 1,730,000 | 18 | 362,000 | 72,000 | 2,363,000 |
| 6 | 728,000 | 96,000 | 2,050,000 | | | | |
| 7 | 486,000 | 147,000 | 1,388,000 | | | | |

-continued

| 3.4 Molecular weight - Comparison | | | | | | | |
|---|---|---|---|---|---|---|---|
| Run | Mw | Mn | Mz | Run | Mw | Mn | Mz |
| 12 | 512,000 | 108,000 | 1,430,000 | 15 | not. det. | not. det. | not. det. |
| 13 | 583,500 | 127,000 | 592,000 | 16 | not. det. | not. det. | not. det. |
| 14 | not. det. | not. det. | not. det. | 17 | not. det. | not. det. | not. det. |

| 3.5 Molecular weight distribution (MWG) & Mooney viscosity - Comparison | | | | | | |
|---|---|---|---|---|---|---|
| Run | Mw/Mn | Mooney | Tg in °C. | Run | Mw/Mn | Mooney | Tg in °C. |
| 1 | 2.8 | 85.3 | −107.2 | 8 | not. det. | 155.3 | not. det. |
| 2 | not. det. | 88.1 | −107.4 | 9 | 5.83 | 87.3 | not. det. |
| 3 | 3.3 | 91.0 | not. det. | 10 | 5.0 | 23.6 | not. det. |
| 4 | 2.5 | 81.3 | not. det. | 11 | 4.0 | 30.5 | not. det. |
| 5 | 3..1 | 112.7 | not. det. | 18 | 5.0 | not. det. | not. det. |
| 6 | 7.6 | not. det. | not. det. | | | | |
| 7 | 3.3 | 54.2 | not. det. | | | | |

| Run | Mw/Mn | Mooney | Tg in °C. | Run | Mw/Mn | Mooney | Tg in °C. |
|---|---|---|---|---|---|---|---|
| 12 | 4.74 | not. det. | not. det. | 15 | not. det. | not. det. | not. det. |
| 13 | 2.23 | 25.8 | not. det. | 16 | not. det. | 33.9 | −106.8 |
| 14 | not.det. | not. det. | not. det. | 17 | not. det. | 38.2 | not. det. |

| 3.6 Microstructure - Polybutadiene Fraction Comparison | | | | | | |
|---|---|---|---|---|---|---|
| Run | Cis-1,4-PB | Trans-1,4-PB | 1,2-PB | Run | Cis-1,4-PB | Trans-1,4-PB | 1,2-PB |
| 1 | 97.3 | 2.0 | 0.7 | 8 | 80.1 | 18.8 | 1.1 |
| 2 | 96.5 | 2.0 | 1.5 | 9 | 83.5 | 15.2 | 1.3 |
| 3 | 97.9 | 1.4 | 0.7 | 10 | 66.6 | 31.8 | 1.5 |
| 4 | 93.0 | 6.1 | 0.9 | 11 | 86.2 | 12.6 | 1.2 |
| 5 | 92.4 | 6.9 | 0.8 | 18 | 85.4* | 13.4* | 1.0* |
| 6 | 95.4 | 3.7 | 0.9 | | | | |
| 7 | 91.5 | 7.8 | 0.8 | | | | |

| Run | Cis-1,4-PB | Trans-1,4-PB | 1,2-PB | Run | Cis-1,4-PB | Trans-1,4-PB | 1,2-PB |
|---|---|---|---|---|---|---|---|
| 12 | 94.0 | 3.0 | 3.0 | 15 | not. det. | not. det. | not. det. |
| 13 | 93.5 | 5.5 | 1.0 | 16 | 69.5 | 12.5 | 8.5 |
| 14 | not. det. | not. det. | not. det. | 17 | 93.7 | 4.7 | 1.7 |

*styrene content amounts to 0.2 percent

The invention claimed is:

1. A metal complex catalyst, which is a reaction product of:
   A) at least one metal complex represented by Formula 3, 4 or 5:

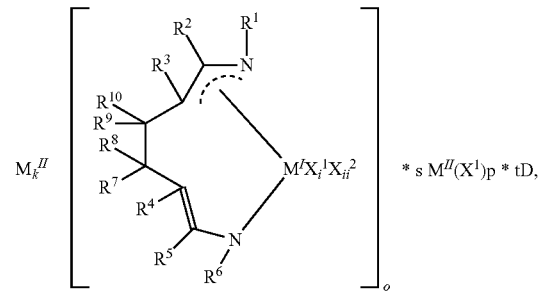

Formula 3

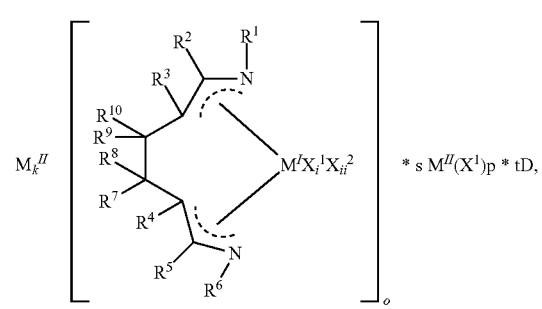

Formula 4

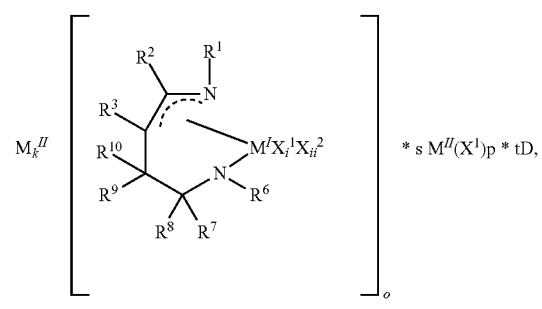

Formula 5 wherein,
$R^1$, $R^2$, $R^3$, $R^4$, $R^5$, $R^6$, $R^7$, $R^8$, $R^9$, $R^{10}$ and $X^2$ are, independently in each occurrence, hydrogen, a halide atom, or a group having from 1 to 80 atoms, not counting hydrogen, selected from hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl;

$M^I$ is lanthanum, cerium, praseodymium, neodymium, or promethium;

$M^{II}$ is lithium, sodium, potassium or magnesium;

N is nitrogen $X^1$ is fluoride, chloride, bromide or iodide;

D is THF, DME or $Et_2O$;

t is the number 0, 1, 2, 3, 4, 5 or 6;

s is the number 0, 1 or 2;

o is the number 1 or 2;
p is the number 1 or 2;
k is the number 0, 1, 2, 3 or 4;
i, ii are the numbers 0, 1 or 2; and the sum of i and ii represents one of the numbers 1, 2 or 3; and
B) at least one activator selected from:
  a) $C_{1-30}$ organoboron or organoaluminum compounds,
  b) polymeric or oligomeric alumoxanes,
  c) non-polymeric compatible, non-coordinating, ion-forming compounds, and
  d) hydrocarbyl sodium, hydrocarbyl lithium, hydrocarbyl zinc, hydrocarbyl magnesium halide, and dihydrocarbyl magnesium; and
wherein A) and B) are brought together in a reaction medium at a temperature from −78° C. to 250° C.

2. The catalyst of claim 1, wherein the reaction medium is selected from at least one of the following: an aliphatic hydrocarbon, an aromatic hydrocarbon or a halohydrocarbon; and at a temperature of from −5° C. to 160° C.

3. The catalyst of claim 1, wherein $M^I$ is neodymium.

4. The catalyst of claim 1, further comprising a support.

5. The catalyst of claim 4, wherein the support is selected from at least one of the following: clay, silica, layered silicates, alumina, activated carbon, graphite or carbon black.

6. The catalyst of claim 1, wherein the activator comprises a combination of the following:
  a) a trialkyl aluminum compound having from 1 to 4 carbon atoms in each alkyl group, and
  b) a halogenated tri(hydrocarbyl)boron compound or halogenated tetrakis(hydrocarbyl)boron or -aluminum compound, each having from 1 to 20 carbon atoms in each hydrocarbyl group.

7. The catalyst of claim 1, wherein the activator comprises a combination of the following:
  a) a tris(pentafluorophenyl)borane, tetrakis(pentafluorophenyl)borate, or tetrakis(3,5-bis(trifluoromethyl)phenyl)borate, and
  b) a polymeric or oligomeric alumoxane.

8. The catalyst of claim 1, wherein the activator comprises a combination of the following:
  a) a trialkyl aluminum or dialkyl aluminum hydride compound, and
  b) boron trifluoride, boron trichloride, boron tribromide, aluminum trifluoride, aluminum trichloride, aluminum tribromide, scandium trifluoride, or titanium tetrafluoride.

* * * * *